United States Patent
Gautron et al.

(10) Patent No.: US 11,414,398 B2
(45) Date of Patent: Aug. 16, 2022

(54) SELECTIVE ORGANIC CATION TRANSPORTERS INHIBITORS FOR THE TREATMENT OF DEPRESSIVE DISORDERS

(71) Applicants: SORBONNE UNIVERSITÉ, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); UNIVERSITE PARIS DESCARTES, Paris (FR)

(72) Inventors: Sophie Gautron, Paris (FR); Nicolas Pietrancosta, Montigny le Bretonneux (FR); Francine Acher, Vaucresson (FR); Laetitia Chausset-Boissarie, Sailly-lez-Lannoy (FR)

(73) Assignees: SORBONNE UNIVERSITÉ, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); UNIVERSITÉ PARIS CITÉ, Paris (FR)

( * ) Notice: Subject to any disclaimer, the term of this patent is extended or adjusted under 35 U.S.C. 154(b) by 59 days.

(21) Appl. No.: 16/630,082

(22) PCT Filed: Jul. 13, 2018

(86) PCT No.: PCT/EP2018/069179
§ 371 (c)(1),
(2) Date: Jan. 10, 2020

(87) PCT Pub. No.: WO2019/012150
PCT Pub. Date: Jan. 17, 2019

(65) Prior Publication Data
US 2020/0199100 A1 Jun. 25, 2020

(30) Foreign Application Priority Data
Jul. 13, 2017 (EP) .................................... 17305935

(51) Int. Cl.
*C07D 401/06* (2006.01)
(52) U.S. Cl.
CPC .................. *C07D 401/06* (2013.01)
(58) Field of Classification Search
CPC .................................................. C07D 401/06
USPC ......................................................... 514/314
See application file for complete search history.

(56) References Cited

U.S. PATENT DOCUMENTS 3,909,275 A 9/1975 Gandino et al.

FOREIGN PATENT DOCUMENTS

DE 41 37 009 5/1993
WO WO 2009/134877 11/2009

OTHER PUBLICATIONS

Dorwald et al., Side reactions in Organic Synthesis, Wiley: VCH Weinheim Preface, pp. 1-15 and Chapter 8, pp. 279-308. (Year: 2005).*
Bacq et al., "Organic cation transporter 2 controls brain norepinephrine and serotonin clearance and antidepressant response," Molecular Psychiatry, 2011, pp. 1-14.
Courousse et al., "Role of organic cation transporters (OCTs) in the brain," Pharmacology & Therapeutics, 2015, vol. 146, pp. 94-103.
Russ et al., "Cyanine-related compounds: a novel class of potent inhibitors of extraneuronal noradrenaline transport," Naunyn-Schmiedeberg's Arch Pharmacol, 1993, vol. 348, pp. 458-465.
Gorbunov et al., "High-Affinity Cation Binding to Organic Cation Transporter 1 Induces Movement of Helix 11 and Blocks Transport after Mutations in a Modeled Interaction Domain between Two Helices," Molecular Pharmacology, 2008, vol. 73, No. 1, pp. 50-61.
Russ et al., "Pharmacokinetic and alpha 1-adrenoceptor antagonistic properties of two cyanine-type inhibitors of extraneuronal monoamine transport," Naunyn-Schmiedeberg's Arch Pharmacol, 1996, vol. 354, pp. 268-274.
Iversen, "The Uptake of Catechol Amines at High Perfusion Concentrations in the Rat Isolated Heart: A Novel Catechol Amine Uptake Process," Brit. J. Pharmacol., 1965, vol. 25, pp. 18-33.

(Continued)

*Primary Examiner* — Taofiq A Solola
(74) *Attorney, Agent, or Firm* — Nixon & Vanderhye

(57) ABSTRACT

Disclosed are organic cation transporters (OCTs) inhibitors of Formula (A), as well as their pharmaceutically acceptable tautomers, salts or solvates.

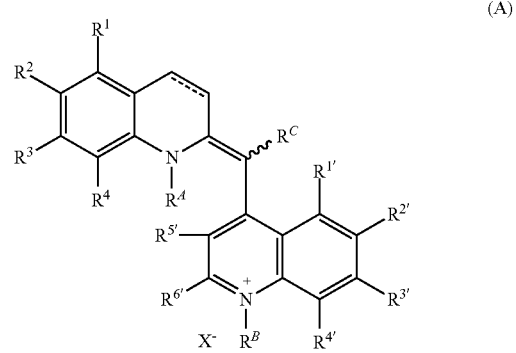

Also disclosed are pharmaceutical compositions including such OCTs inhibitor of Formula (A) and their use for treating and/or preventing mood-related disorders such as depressive disorders.

12 Claims, 7 Drawing Sheets

(56) References Cited

OTHER PUBLICATIONS

Wilson et al., "The uptake and O-methylation of 3H-(+/−)-isoprenaline in rat cerebral cortex slices," Naunyn-Schmiedeberg's Arch Pharmacol, 1988, vol. 337, pp. 397-405.
Foucout et al., "Synthesis, radiosynthesis and biological evaluation of 1,4-dihydroquinoline derivatives as new carriers for specific brain delivery," Organic & Biomolecular Chemistry, 2009, vol. 7, pp. 3666-3673.
Berton et al., "Essential Role of BDNF in the Mesolimbic Dopamine Pathway in Social Defeat Stress," Science, Feb. 10, 2006, vol. 311, pp. 864-868.
Bradely et al., "Action of Reagents and Dialkylcadmiums on Alkylquinolinium and Alkylisoquinolinium Salts. A Relation between the Basic Strength of Anions and their Orientation in Nuclear Substitution Reaction," J., Chem. Soc., 1954, pp. 2770-2778.
Lartia et al., "New Cyanine-Oligonucleotide Conjugates: Relationships between Chemical Structures and Properties," Chem. Eur. J., 2006, vol. 12, pp. 2270-2281.
International Search Report, PCT/EP2018/069179, dated Oct. 10, 2018.
Anne Amphoux et al: "Inhibitory and facilitory actions of isocyanine derivatives at human and rat organic cation transporters 1, 2 and 3: A comparison to human [alpha]1- and [alpha]2-adrenoceptor subtypes". European Journal of Pharmacology, vol. 634. No. 1-3. May 1, 2010 (May 1, 2010) pp. 1-9, XP055436669, NL, ISSN: 0014-2999. DOI:10.1016/j.ejphar.2010.02.012, figure 1.
Written Opinion, PCT/EP2018/069179, dated Oct. 10, 2018.

\* cited by examiner

SELECTIVE ORGANIC CATION TRANSPORTERS INHIBITORS FOR THE TREATMENT OF DEPRESSIVE DISORDERS

FIELD OF INVENTION

The present invention relates to novel quinolinium derivatives of Formula (I), including pharmaceutically acceptable tautomers, salts or solvates thereof. Compounds of the invention are inhibitors of organic cation transporters (OCTs) and are useful as therapeutic compounds, particularly in the treatment and/or prevention of depressive disorders and other mood-related disorders such as anxiety-related disorders.

BACKGROUND OF INVENTION

Mood disorders represent widespread and invalidating disorders, with up to 16% of the world population affected by various symptoms of the depression spectrum. However current treatments, which mainly act on monoamine neurotransmission, have major drawbacks, such as slow speed of action, poor efficacy and unwanted side-effects. Moreover, these treatments do not provide positive treatment outcomes for an important fraction of patients (so called "resistant depression").

Consequently, there is a need to develop novel antidepressant compounds, in the field of mood disorders treatments.

Fundamental and preclinical studies have identified the importance of a category of monoamine transporters, organic cation transporters (OCTs), in mood-related behaviors. Two OCT subtypes, OCT2 and OCT3, are expressed in the central nervous system where they contribute to shape mood-related functions such as anxiety, response to stress and antidepressant efficacy (Bacq et al., Mol. Psychiatry, 2012, 17, 926-939; Couroussé et al., Pharmacol. Therapeutics, 2015, 146, 94-103). Contrasting with the high-affinity transporters gathered in aminergic terminals, OCT2 and OCT3 are also found throughout the brain in the principal regions receiving aminergic projections.

The Applicant speculated that manipulation of central OCT-mediated transport activity could exert antidepressant effects by engaging different mechanisms than those resulting from high-affinity transporter blockade.

In this context, the Applicant selected a known potent OCT inhibitor, disprocynium 24 (D24), as lead compound for pharmacomodulation studies.

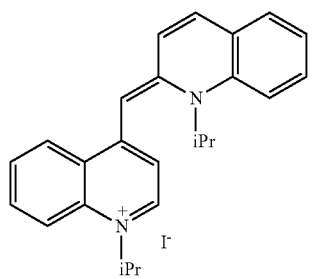

D24

D24 is the most selective among the potent inhibitors of OCTs identified to date (Ki=14 nM for OCT3) (Russ et al., Arch. Pharmacol., 1993, 348, 458-465), interacting with a putative high-affinity binding site of these transporters (Gorbunov et al., Molecular Pharmacol., 2008, 73, 50-61).

However, D24 presents some important limitations while used in vivo in preclinical or clinical studies. D24 inhibits α1 and α2-adrenoreceptors (Amphoux et al., Eur. J. Pharmacol., 2010, 634, 1-9), therefore it leads to important effects on peripheral organs. Especially, D24 was evidenced to have hypotensive effects by decreasing blood pressure markedly after injection in rabbits (Russ et al., Arch Pharmacol., 1996, 354, 268-274). Furthermore, this type of compound is believed to diffuse poorly across the brain blood barrier, and could target uptake$_2$, an OCT-mediated catecholamine clearance system found in sympathetically-innervated organs and tissues (Iversen, Brit. J. Pharmacol., 1965, 25, 18-33; Wilson et al., Arch. Pharmacol., 1988, 337, 397-405).

In the present invention, the Applicant provides analogs of D24 and prodrugs thereof. The prodrugs of the invention, which are reduced forms of the active analogs of D24, should be able to readily diffuse into the brain parenchyma and be activated therein by oxidation.

The activated drugs (oxidized forms) corresponding to the prodrugs of the invention (reduced form) have an improved affinity for OCTs and an improved selectivity for OCTs over adrenergic receptors, compared to D24.

Besides, the compounds of the invention display limited, if any, toxic and/or side effects and no lethality at high doses.

The compounds of the invention were evaluated in vivo in mice for behavioral effects, in particular for antidepressant efficacy in a validated chronic depression model. As evidenced in the experimental part below, the compounds of the invention show antidepressant efficacy with rapid positive effects. Especially, the Applicant evidenced a strong efficacy for compounds tested alone, an improved speed of action on anhedonia and better action on anxiety, compared to one commonly used antidepressant, fluoxetine. In addition, the compounds of the invention appear to be less hepatotoxic than fluoxetine and could have less anorectic effects.

SUMMARY

This invention thus relates to a compound of Formula (I)

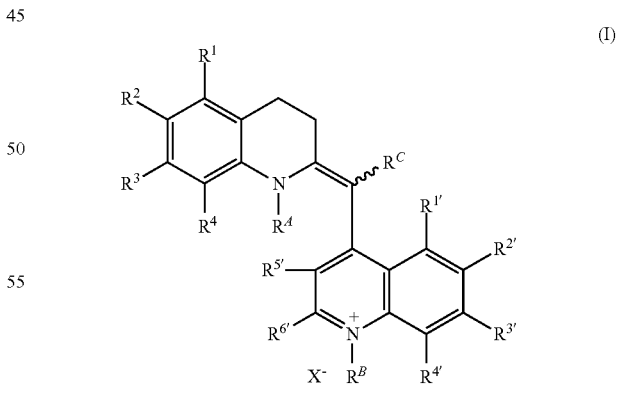

(I)

or a pharmaceutically acceptable tautomer, salt or solvate thereof, wherein: ∼∼, X, $R^A$, $R^B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined hereafter.

According to one embodiment, the compound of Formula (I) is of Formula (Ia) or (Ib) as defined hereafter. According to one embodiment, the compound of Formula (I) is of Formula (I-1) as defined hereafter. According to one embodiment, the compound of Formula (I) is Formula (Ia-1) or (Ib-1) as defined hereafter.

According to one embodiment, the compound of Formula (I) is selected from the group consisting of:
(Z)-1-isopropyl-4-((1-isopropyl-6-methoxy-3,4-dihydroquinolin-2(1H)-ylidene)methyl)quinolin-1-ium iodide;
(Z)-1-isopropyl-4-((1-isopropyl-6-methoxy-3,4-dihydroquinolin-2(1H)-ylidene)(methoxy)methyl)quinolin-1-ium iodide;
and pharmaceutically acceptable tautomers, salts and solvates thereof.

The invention also relates to a pharmaceutical composition comprising a compound of Formula (I), or a pharmaceutically acceptable tautomer, salt or solvate thereof, and at least one pharmaceutically acceptable carrier.

The invention also relates to a medicament comprising a compound of Formula (I), or a pharmaceutically acceptable tautomer, salt or solvate thereof.

The invention further relates to a compound of Formula (I), or a pharmaceutically acceptable tautomer, salt or solvate thereof for use in the treatment and/or prevention of depressive disorders and anxiety disorders.

The invention also relates to a compound of Formula (I), or a pharmaceutically acceptable tautomer, salt or solvate thereof for use as organic cation transporters (OCTs) inhibitor.

It is also an object of the invention to provide a process for manufacturing a compound of Formula (I) or a pharmaceutically acceptable tautomer, salt or solvate thereof, characterized in that it comprises the regioselective reduction of intermediate of Formula (II)

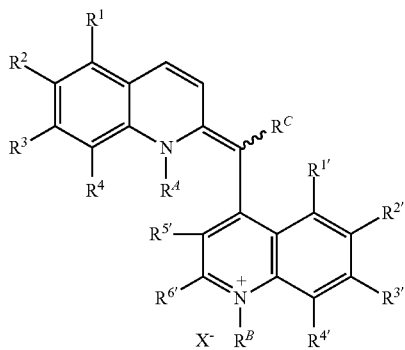

(II)

wherein ⌇⌇⌇, X, $R^A$, $R_B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined hereafter;
in presence of sodium dithionite ($Na_2S_2O_4$).

According to one embodiment, the process of the invention comprises a preliminary step of synthesis of intermediate of Formula (II) comprising the coupling between intermediate of Formula (III) and intermediate of Formula (IV), in presence of a base:

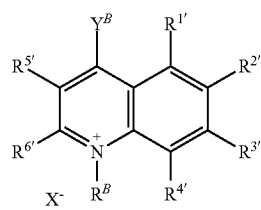

(III)

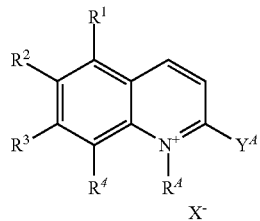

(IV)

wherein $R^A$, $R^B$, $R^1$, $R^2$, $R^3$, $R^4$, $R^{1'}$, $R^{2'}$, $R^{3'}$, $R^{4'}$, $R^{5'}$ and $R^{6'}$ are as defined in claim 1; and
$Y^A$ is —$CH_2R^C$, wherein $R^C$ is as defined in Formula (I); and $Y^B$ is hydrogen or a leaving group preferably selected from halo, acetate, tosylate, mesylate and sulfate; preferably in such case $Y^B$ is halo; more preferably, $Y^B$ is Cl;
or
$Y^A$ is hydrogen or a leaving group preferably selected from halo, acetate, tosylate, mesylate and sulfate; and $Y^B$ is —$CH_2R^C$, wherein $R^C$ is as defined in Formula (I); preferably in such case $Y^A$ is halo; more preferably $Y^A$ is Cl.

The invention also relates to a compound of Formula (II)

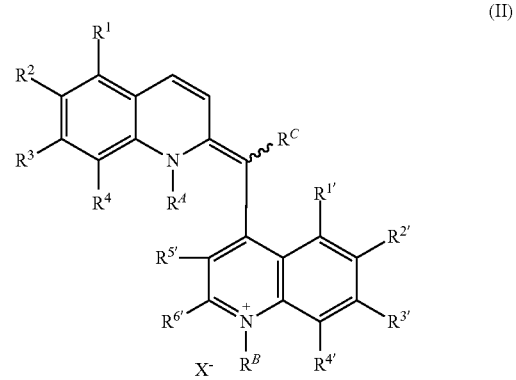

(II)

or a pharmaceutically acceptable tautomer, salt or solvate thereof, wherein: ⌇⌇⌇, X, $R^A$, $R^B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined hereafter.

According to one embodiment, the compound of Formula (II) is selected from the group consisting of:

(Z)-1-isopropyl-4-((1-isopropyl-6-methoxyquinolin-2 (1H)-ylidene)methyl)quinolin-1-ium iodide;

(Z)-1-isopropyl-4-((1-isopropyl-6-methoxyquinolin-2 (1H)-ylidene)(methoxy)methyl)quinolin-1-ium iodide;

and pharmaceutically acceptable tautomers, salts and solvates thereof.

Definitions

In the present invention, the following terms have the following meanings:

The term "alkoxy" refers to a group —O-alkyl wherein alkyl is as herein defined.

The term "alkyl" refers to a hydrocarbyl radical of formula $C_nH_{2n+1}$ wherein n is a number greater than or equal to 1. Generally, alkyl groups of this invention comprise from 1 to 8 carbon atoms, more preferably, alkyl groups of this invention comprise from 1 to 6 carbon atoms. Alkyl groups may be linear or branched. Suitable alkyl groups include methyl, ethyl, propyl, butyl, pentyl, hexyl, heptyl and octyl.

The term "alkylamino" refers to a group —NH-alkyl wherein alkyl is as herein defined.

The term "alkyloxycarbonyl" refers to a group —(C=O)—O-alkyl wherein alkyl is as herein defined.

The term "amino" refers to a group —NH$_2$.

The term "aminoalkyl" refers to a group -alkyl-NH$_2$ wherein alkyl is as herein defined.

The term "aryl" refers to a polyunsaturated, aromatic hydrocarbyl group having a single ring (i.e. phenyl) or multiple aromatic rings fused together (e.g. naphtyl), typically containing 5 to 12 atoms; preferably 5 to 10; more preferably the aryl is a 5- or 6-membered aryl. Non-limiting examples of aryl comprise phenyl, naphthalenyl.

The term "cycloalkyl" refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms; still more preferably more preferably the cycloalkyl is a 5- or 6-membered cycloalkyl. Examples of cycloalkyl groups include but are not limited to cyclopropyl, cyclobutyl, cyclopentyl, cyclohexyl.

The term "halo" or "halogen" refers to fluoro, chloro, bromo, or iodo.

The term "haloalkyl" refers to any alkyl group substituted by one or more halo group. Examples of preferred haloalkyl groups are $CF_3$, $CHF_2$ and $CH_2F$.

The term "haloalkyloxy" refers to a group —O-haloalkyl wherein haloalkyl is as herein defined.

The term "heteroaryl" refers to an aryl group as herein defined wherein at least one carbon atom is replaced with a heteroatom. In other words, it refers to 5 to 12 carbon-atom aromatic single rings or ring systems containing 2 rings which are fused together, typically containing 5 to 6 atoms; in which one or more carbon atoms is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1 (2H)-yl, 6-oxo-pyrudazin-1(6H)-yl, 2-oxopyridin-1(2H)-yl, 1,3-benzodioxolyl, quinolinyl, isoquinolinyl, cinnolinyl, quinazolinyl, quinoxalinyl.

The term "heterocyclyl" refers to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Preferably the heterocyclyl is a 5- or 6-membered heterocyclyl. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, 1-oxido-1-thiomorpholin-4-yl, 1-dioxido-1-thiomorpholin-4-yl, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

The term "tautomer" refers to constitutional isomers of organic compounds that readily interconvert in a rapid equilibrium by the relocation of a proton. For example, Formula (I') represented below is a tautomeric form of Formula (I):

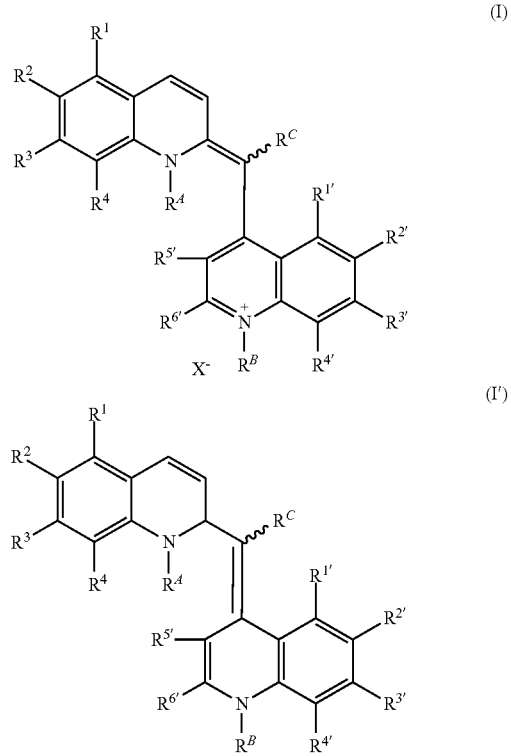

The term "administration", or a variant thereof (e.g. "administering"), means providing the active agent or active ingredient (e.g. an inhibitor of organic cation transporters (OCTs)), alone or as part of a pharmaceutically acceptable composition, to the patient in whom/which the condition, symptom, or disease is to be treated or prevented.

The terms "$IC_{50}$" or "half maximal inhibitory concentration" represent the concentration of an inhibitor that is required for 50% inhibition in vitro.

The term "inhibitor" refers to a natural or synthetic compound that has a biological effect to inhibit or significantly reduce or down-regulate the expression of a gene and/or a protein or that has a biological effect to inhibit or significantly reduce the biological activity of a protein. Consequently, an "OCT inhibitor" refers to a compound that has a biological effect to inhibit or significantly reduce or down-regulate the biological activity of OCTs transporters.

The term "human" refers to a subject of both genders and at any stage of development (i.e. neonate, infant, juvenile, adolescent, adult).

The term "patient" refers to a warm-blooded animal, more preferably a human, who/which is awaiting the receipt of, or is receiving medical care or is/will be the object of a medical procedure.

The expression "pharmaceutically acceptable" refers to the ingredients of a pharmaceutical composition are compatible with each other and not deleterious to the subject to which it is administered.

The expression "pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The terms "treating" or "treatment" refer to both therapeutic treatment and prophylactic or preventative measures; wherein the object is to prevent or slow down the targeted pathologic condition or disease. Those in need of treatment include those already with the disease as well as those prone to have the disease or those in whom the disease is to be prevented. A subject or mammal is successfully "treated" for a disease or affection or condition if, after receiving the treatment according to the present invention, the subject or mammal shows observable and/or measurable reduction in or absence of one or more of the following: reduction of depression symptoms; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

The expression "depressive disorders" refers to disorders including disruptive mood dysregulation disorder, major depressive disorder (including major depressive episode), persistent depressive disorder (dysthymia), premenstrual dysphoric disorder, substance/medication-induced depressive disorder, depressive disorder due to another medical condition, other specified depressive disorder, and unspecified depressive disorder (Diagnostic and Statistical Manual of Mental Disorders, Fifth Edition).

The expression "anxiety disorders" refers to disorders including separation anxiety disorder, selective mutism, specific phobia, social anxiety disorder (Social phobia), panic disorder, panic attack specifier, agoraphobia, generalized anxiety disorder, substance or medication-induced anxiety disorder, anxiety disorder due to a medical condition, other specified anxiety disorder, unspecified anxiety disorder (Diagnostic and Statistical Manual of Mental Disorders, Fifth Edition).

DETAILED DESCRIPTION

This invention relates to compounds of general Formula (A)

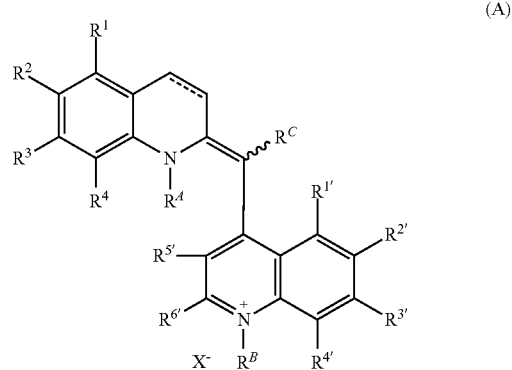

(A)

or a pharmaceutically acceptable tautomer, salt or solvate thereof, wherein:

represents a single bond or a double bond;

represents a single bond linking $R^C$ to the double bond either with a (Z)- or (E)-stereochemistry;

X represents halo, acetate, trifluoroacetate or triflate;

$R^A$ and $R^B$ are independently selected from alkyl;

$R^C$ represents hydrogen, alkyl, alkoxy or haloalkyl;

$R^1$, $R^2$, $R^3$ and $R^4$ are independently selected from hydrogen, hydroxyl, alkoxy, halo, haloalkyl, haloalkyloxy, amino, alkylamino, aminoalkyl, alkyloxycarbonyl and COOH; or $R^1$ and $R^2$, or $R^2$ and $R^3$, or $R^3$ and $R^4$ form together with the carbon atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH;

$R^{1'}$, $R^{2'}$, $R^{3'}$, $R^{4'}$, $R^{5'}$ and $R^{6'}$ are independently either absent or selected from hydrogen, hydroxyl, alkoxy, halo, haloalkyl, haloalkyloxy, amino, alkylamino, aminoalkyl, alkyloxycarbonyl and COOH; or $R^{1'}$ and $R^{2'}$, or $R^{2'}$ and $R^{3'}$, or $R^{3'}$ and $R^{4'}$, or $R^{5'}$ and $R^{6'}$, form together with the carbon atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH;

or $R^4$ and $R^{5'}$ form together with atoms to which they are attached a 6-membered heteroaryl ring optionally substituted by one or more substituent selected from alkyl, hydroxyl, alkoxy, halo, haloalkyl, haloalkyloxy, amino, alkylamino, aminoalkyl, alkyloxycarbonyl and COOH;

wherein at least one of $R^1$, $R^2$, $R^3$, $R^4$, $R^{1'}$, $R^{2'}$, $R^{3'}$, $R^{4'}$, $R^{5'}$ or $R^{6'}$ is other than hydrogen.

The invention especially relates to compounds of Formula (I) and of Formula (II) as described below:

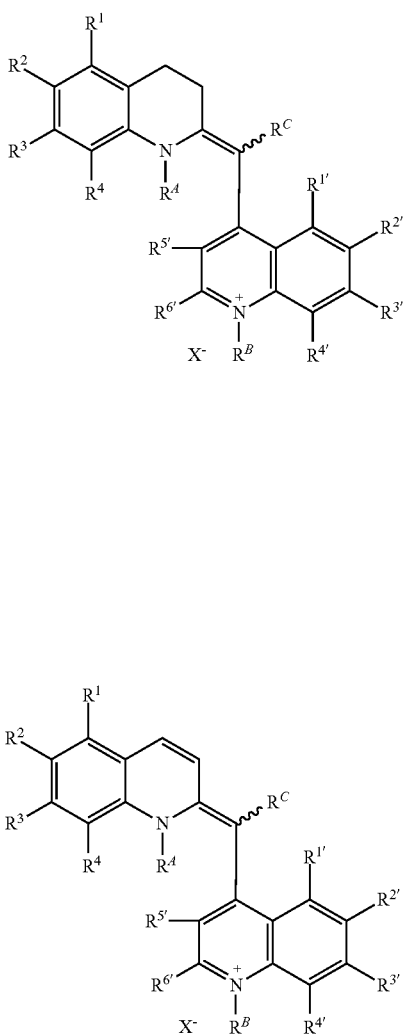

or a pharmaceutically acceptable tautomer, salt or solvate thereof, wherein ⌇⌇⌇, X, $R^A$, $R^B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined in Formula (A).

Compounds of Formula (I) correspond to the reduced form of compounds of Formula (II). Compounds of Formula (II) are deemed to be the active forms in vivo, while reduced compounds of Formula (I) correspond to prodrugs thereof which enable diffusion into the brain after administration.

This invention thus relates to compounds of Formula (I)

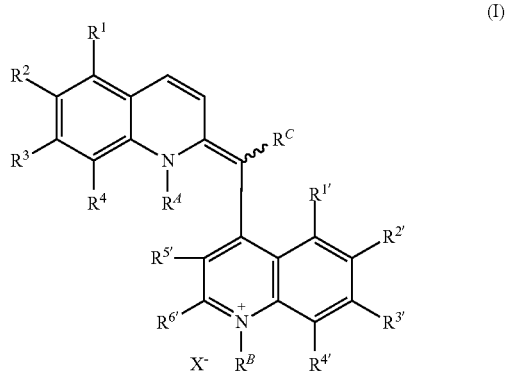

or a pharmaceutically acceptable tautomer, salt or solvate thereof, wherein:
⌇⌇⌇ represents a single bond linking $R^C$ to the double bond either with a (Z)- or (E)-stereochemistry;
X represents halo, acetate, trifluoroacetate or triflate;
$R^A$ and $R^B$ are independently selected from alkyl;
$R^C$ represents hydrogen, alkyl, alkoxy or haloalkyl;
$R^1$, $R^2$, $R^3$ and $R^4$ are independently selected from hydrogen, hydroxyl, alkoxy, halo, haloalkyl, haloalkyloxy, amino, alkylamino, aminoalkyl, alkyloxycarbonyl and COOH; or $R^1$ and $R^2$, or $R^2$ and $R^3$, or $R^3$ and $R^4$ form together with the carbon atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH;
$R^{1'}$, $R^{2'}$, $R^{3'}$, $R^{4'}$, $R^{5'}$ and $R^{6'}$ are independently either absent or selected from hydrogen, hydroxyl, alkoxy, halo, haloalkyl, haloalkyloxy, amino, alkylamino, aminoalkyl, alkyloxycarbonyl and COOH; or $R^{1'}$ and $R^{2'}$, or $R^{2'}$ and $R^{3'}$, or $R^{3'}$ and $R^{4'}$, or $R^{5'}$ and $R^{6'}$, form together with the carbon atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH;
or $R^4$ and $R^{5'}$ form together with atoms to which they are attached a 6-membered heteroaryl ring optionally substituted by one or more substituent selected from alkyl, hydroxyl, alkoxy, halo, haloalkyl, haloalkyloxy, amino, alkylamino, aminoalkyl, alkyloxycarbonyl and COOH;
wherein at least one of $R^1$, $R^2$, $R^3$, $R^4$, $R^{1'}$, $R^{2'}$, $R^{3'}$, $R^{4'}$, $R^{5'}$ or $R^{6'}$ is other than hydrogen.

In one embodiment of the invention, X represents a halo, acetate, trifluoroacetate or triflate. In a specific embodiment, X represents halo, preferably iodo.

In one embodiment of the invention, $R^A$ and $R^B$ are identical. In another embodiment, $R^A$ and $R^B$ are different. In a specific embodiment, $R^A$ and $R^B$ both represent isopropyl.

In a specific embodiment of the invention, $R^C$ represents hydrogen, methyl, methoxy or trifluoromethyl, preferably $R^C$ represents hydrogen.

In one embodiment of the invention, $R^1$, $R^2$, $R^3$ and $R^4$ are independently selected from hydrogen, hydroxyl, alkoxy, halo, haloalkyl, haloalkyloxy, amino, alkylamino, aminoalkyl, alkyloxycarbonyl and COOH. In a preferred embodiment, $R^1$, $R^2$, $R^3$ and $R^4$ are independently selected from H, —OH, —OCH$_3$, F, Cl, —CF$_3$, —OCF$_3$, —NHR or —COOR, wherein R represents hydrogen or alkyl.

In a specific embodiment, $R^4$ is H. In a preferred embodiment, $R^1$, $R^3$ and $R^4$ are H and $R^2$ is selected from hydrogen, hydroxyl, alkoxy, halo, haloalkyl, haloalkyloxy, amino, alkylamino, aminoalkyl, alkyloxycarbonyl and COOH. In a more a preferred embodiment, $R^1$, $R^3$ and $R^4$ are H and $R^2$ is selected from H, —OH, —OCH$_3$, F, Cl, —CF$_3$, —OCF$_3$, —NHR or —COOR, wherein R represents hydrogen or alkyl.

In an alternative embodiment, $R^1$, $R^2$, $R^3$ and $R^4$ are all hydrogen atoms, when at least one of $R^{1'}$, $R^{2'}$, $R^{3'}$, $R^{4'}$, $R^{5'}$ and $R^{6'}$ is other than hydrogen.

In another embodiment of the invention, $R^1$ and $R^2$, or $R^2$, and $R^3$, or $R^3$, and $R^4$ form together with the atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH. In a preferred embodiment, $R^1$ and $R^2$ form together with the atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH, and $R^3$ and $R^4$ are H. In another preferred embodiment, $R^1$ and $R^2$ form together with the atoms to which they are attached a 6-membered aryl ring optionally substituted by one or more substituent selected from hydrogen, hydroxyl, alkoxy, halo, haloalkyl, haloalkyloxy, amino, alkylamino, aminoalkyl, alkyloxycarbonyl and COOH, and $R^3$ and $R^4$ are H.

In one embodiment of the invention, $R^{1'}$, $R^{2'}$, $R^{3'}$, $R^{4'}$, $R^{5'}$ and $R^{6'}$ are independently selected from hydrogen, hydroxyl, alkoxy, halo, haloalkyl, haloalkyloxy, amino, alkylamino, aminoalkyl, alkyloxycarbonyl and COOH. In a preferred embodiment, $R^{1'}$, $R^{2'}$, $R^{3'}$, $R^{4'}$, $R^{5'}$ and $R^{6'}$ are independently selected from H, —OH, —OCH$_3$, F, Cl, —CF$_3$, —OCF$_3$, —NHR or —COOR, wherein R represents hydrogen or alkyl.

In a specific embodiment, $R^{1'}$, $R^{2'}$, $R^{3'}$, $R^{4'}$, $R^{5'}$ and $R^{6'}$ and $R^{7'}$ are hydrogen atoms when at least one of $R^1$, $R^2$, $R^3$ and $R^4$ is other than hydrogen.

According to one embodiment, the compounds of the invention may exist as mixture of Z- and E-diastereoisomers. In a specific embodiment of the invention, preferred compounds of Formula (I) are those of Formulae (Ia) and (Ib):

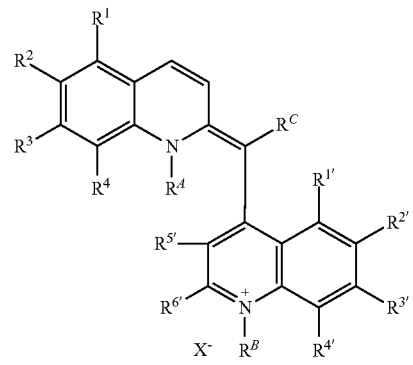

(Ia)

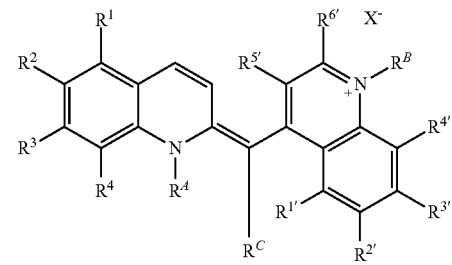

(Ib)

or a pharmaceutically acceptable tautomer, salt or solvate thereof, wherein X, $R^A$, $R^B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined in Formula (I).

According to another specific embodiment, preferred compounds of Formulae (Ia) and (Ib) are those wherein $R^1$, $R^3$, $R^4$, $R^{1'}$, $R^{2'}$, $R^{3'}$, $R^{4'}$, $R^{5'}$ and $R^{6'}$ are hydrogen atoms and $R^2$ is as defined in formula (I).

According to another specific embodiment, preferred compounds of Formulae (Ia) and (Ib) are those wherein $R^1$, $R^2$, $R^3$, $R^4$, $R^{1'}$, $R^{3'}$, $R^{4'}$, $R^{5'}$ and $R^{6'}$ are hydrogen atoms, and $R^{2'}$ is as defined in formula (I).

In one embodiment of the invention, preferred compounds of Formula (I) are those of Formula (I-1)

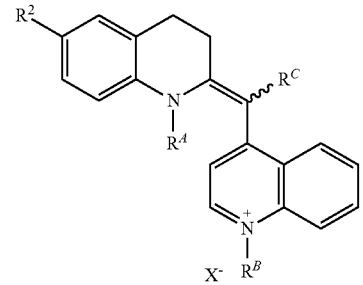

(I-1)

or a pharmaceutically acceptable tautomer, salt or solvate thereof, wherein ⁓, X, $R^A$, $R^B$, $R^C$ and $R^2$ are as defined in Formula (I).

In a specific embodiment of the invention, preferred compounds of Formula (Ia-1) are those of Formulae (Ia-1) and (Ib-1):

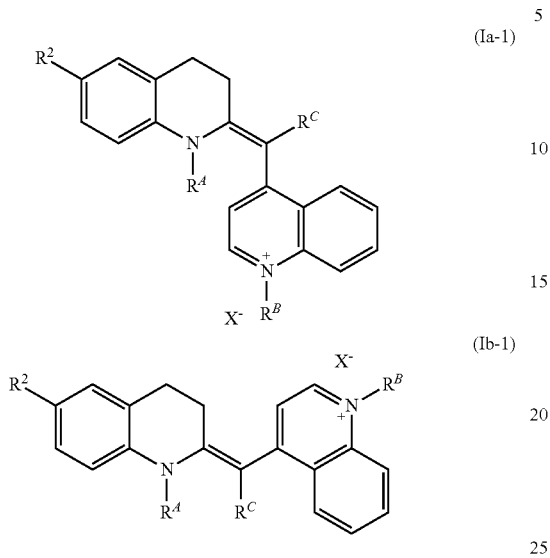

(Ia-1)

(Ib-1)

or a pharmaceutically acceptable tautomer, salt or solvate thereof, wherein X, $R^A$, $R^B$, $R^C$ and $R^2$ are as defined in Formula (I).

Particularly preferred compounds of Formula I of the invention are those listed in Table 1 hereafter.

TABLE 1

| Cpd No. | Structure | Chemical name | MW |
|---|---|---|---|
| I-1 | 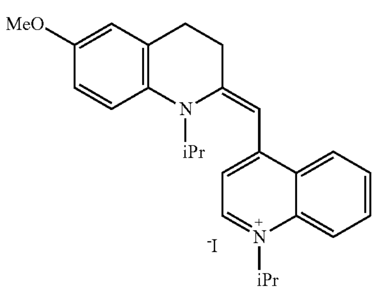 | (Z)-1-isopropyl-4-((1-isopropyl-6-methoxy-3,4-dihydroquinolin-2(1H)-ylidene)methyl)quinolin-1-ium iodide | 514.45 |
| I-2 | | (Z)-1-isopropyl-4-((1-isopropyl-6-methoxy-3,4-dihydroquinolin-2(1H)-ylidene)(methoxy)methyl)quinolin-1-ium iodide | 544.47 | and pharmaceutically acceptable tautomers, salts and solvates thereof.

In Table 1, the term "Cpd" means compound. The compounds of Table 1 were named using ChemBioDraw® Ultra version 12.0 (PerkinElmer).

This invention also relates to compounds of Formula (II), which are oxidized forms of compounds of Formula (I):

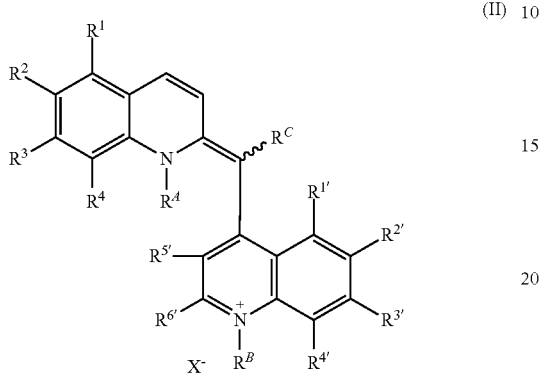

or a pharmaceutically acceptable tautomer, salt or solvate thereof, wherein:

⁓ represents a single bond linking $R^C$ to the double bond either with a (Z)- or (E)-stereochemistry;

X represents halo, acetate, trifluoroacetate or triflate;

$R^A$ and $R^B$ are independently selected from alkyl;

$R^C$ represents hydrogen, alkyl, alkoxy or haloalkyl;

$R^1$, $R^2$, $R^3$ and $R^4$ are independently selected from hydrogen, hydroxyl, alkoxy, halo, haloalkyl, haloalkyloxy, amino, alkylamino, aminoalkyl, alkyloxycarbonyl and COOH; or $R^1$ and $R^2$, or $R^2$ and $R^3$, or $R^3$ and $R^4$ form together with the carbon atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH;

$R^{1'}$, $R^{2'}$, $R^{3'}$, $R^{4'}$, $R^{5'}$ and $R^{6'}$ are independently either absent or selected from hydrogen, hydroxyl, alkoxy, halo, haloalkyl, haloalkyloxy, amino, alkylamino, aminoalkyl, alkyloxycarbonyl and COOH; or $R^{1'}$ and $R^{2'}$, or $R^{2'}$ and $R^{3'}$, or $R^{3'}$ and $R^{4'}$, or $R^{5'}$ and $R^{6'}$, form together with the carbon atoms to which they are attached a 5- or 6-membered aryl ring, a 5- or 6-membered heteroaryl ring, a 5- or 6-membered cycloalkyl ring, a 5- or 6-membered heterocyclyl ring, said rings being optionally substituted by one or more substituent selected from hydroxyl, alkoxy, halo, haloalkyl, haloalkyloxy, amino, alkylamino, aminoalkyl, alkyloxycarbonyl and COOH;

or $R^A$ and $R^{5'}$ form together with atoms to which they are attached a 6-membered heteroaryl ring optionally substituted by one or more substituent selected from alkyl, hydroxyl, alkoxy, halo, haloalkyl, haloalkyloxy, amino, alkylamino, aminoalkyl, alkyloxycarbonyl and COOH;

wherein at least one of $R^1$, $R^2$, $R^3$, $R^4$, $R^{1'}$, $R^{2'}$, $R^{3'}$, $R^{4'}$, $R^{5'}$ or $R^{6'}$ is other than hydrogen.

Preferred embodiments defined above with respect to Formula (I) also apply for compounds of Formula (II). Especially, the compounds of Formula (II) may exist as mixture of Z- and E-diastereoisomers.

Particularly preferred of Formula (II) of the invention are those listed in Table 2 hereafter.

TABLE 2

| Cpd No. | Structure | Chemical name | MW |
|---|---|---|---|
| II-1 | 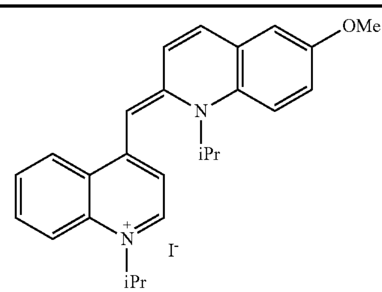 | (Z)-1-isopropyl-4-((1-isopropyl-6-methoxyquinolin-2(1H)-ylidene)methyl)quinolin-1-ium iodide | 512.43 |
| I-2 | | (Z)-1-isopropyl-4-((1-isopropyl-6-methoxyquinolin-2(1H)-ylidene)(methoxy)methyl)quinolin-1-ium iodide | 544.47 | and pharmaceutically acceptable tautomers, salts and solvates thereof.

All references to compounds of Formulae (A), (I), (II) and subformulae thereof include references to isomers (including optical, geometric and tautomeric isomers) salts, solvates, isotopically-labeled compounds, polymorphs, crystals, multi-component complexes and liquid crystals thereof.

The compounds of Formulae (A), (I), (II) and subformulae thereof may contain an asymmetric center and thus may exist as different stereoisomeric forms, especially the Z and E diastereoisomers of the double bond linking the two rings. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of pharmaceutically acceptable salts. Pharmaceutically salts of the compounds of Formulae (A), (I), (II) and subformulae thereof include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formulae (A), (I), (II) and subformulae thereof may be prepared by one or more of these methods:
(i) by reacting the compound with the desired acid;
(ii) by reacting the compound with the desired base;
(iii) by removing an acid- or base-labile protecting group from a suitable precursor of the compound or by ring-opening a suitable cyclic precursor, for example, a lactone or lactam, using the desired acid; or
(iv) by converting one salt of the compound to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of the invention.

The compounds of the invention may be in the form of pharmaceutically acceptable solvates. Pharmaceutically acceptable solvates of the compounds of For Formulae (A), (I), (II) and subformulae thereof contains stoichiometric or sub-stoichiometric amounts of one or more pharmaceutically acceptable solvent molecule such as ethanol or water. The term "hydrate" refers to when the said solvent is water.

The compounds of Formula (I) can be prepared by different ways with reactions known to a person skilled in the art.

The invention further relates to a process for manufacturing of compounds of Formula (I) or a pharmaceutically acceptable tautomer, salt or solvate thereof, characterized in that it comprises the regioselective reduction of compound of Formula (II)

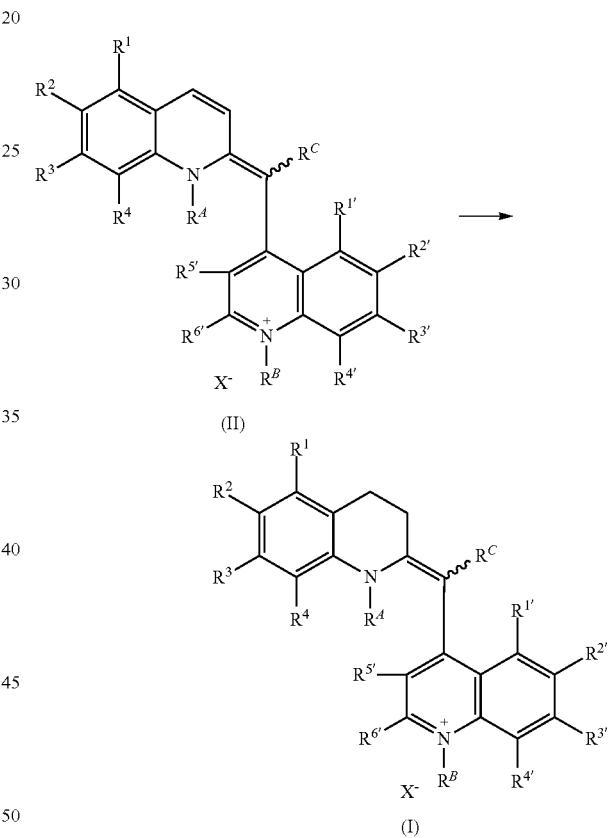

wherein $\sim\!\!\sim$, X, $R^A$, $R^B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined in Formula (I).

According to one embodiment, the regioselective reduction may be performed in the presence of sodium dithionite ($Na_2S_2O_4$).

According to one embodiment, the regioselective reduction may be performed in the presence of one or more suitable deaerated solvents such as, but not limited to, water, $CH_3CN$, methanol, ethanol or mixture thereof; preferably in a mixture of water and $CH_3CN$; even more preferably in a mixture of water and $CH_3CN$ (1:1).

According to one embodiment, the regioselective reduction is preferably performed at room temperature, for a period ranging from 0.1 to 48 hours, preferably at room temperature for 4 h.

According to one embodiment, the regioselective reduction may be performed under inert atmosphere, preferably under nitrogen.

According to one embodiment, the process of the invention comprises a preliminary step of synthesis of intermediate of Formula (II), comprising the coupling between the intermediate of Formula (III) and intermediate of Formula (IV):

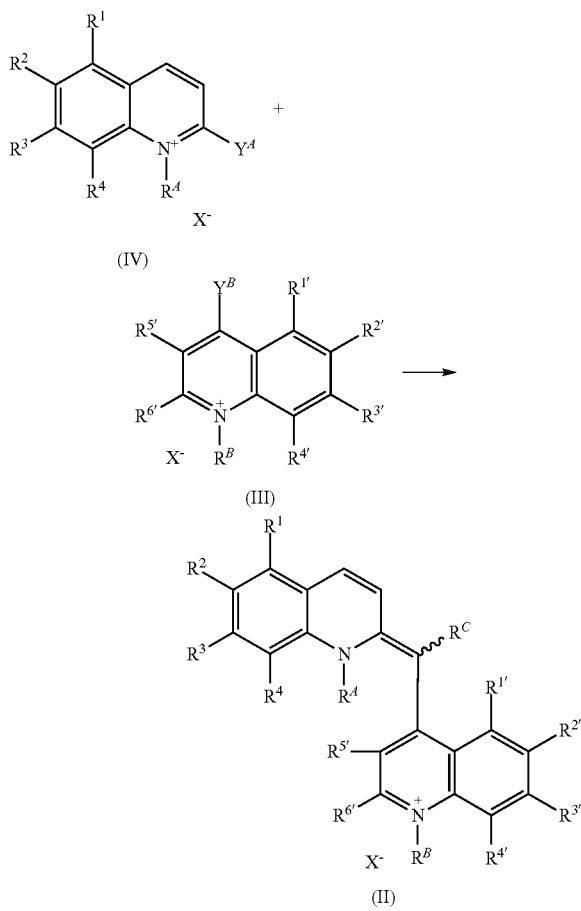

wherein ⁓, X, $R^A$, $R^B$, $R^1$, $R^2$, $R^3$, $R^4$, $R^{1'}$, $R^{2'}$, $R^{3'}$, $R^{4'}$, $R^{5'}$ and $R^{6'}$ are as defined in Formula (I); and $Y^A$ is —$CH_2R^C$, wherein $R^C$ is as defined in Formula (I); and $Y^B$ is hydrogen or a leaving group preferably selected from halo, acetate, tosylate, mesylate and sulfate; preferably in such case $Y^B$ is halo; more preferably, $Y^B$ is Cl;

or $Y^A$ is hydrogen or a leaving group preferably selected from halo, acetate, tosylate, mesylate and sulfate; and $Y^B$ is —$CH_2R^C$, wherein $R^C$ is as defined in Formula (I); preferably in such case $Y^A$ is halo; more preferably $Y^A$ is Cl.

By "leaving group", it is herein referred to groups that are able to depart from the molecule with a pair of electrons in heterolytic bond cleavage. According to a preferred embodiment, examples of leaving groups are preferably selected from halo, acetate, tosylate, mesylate and sulfate groups.

According to one embodiment, the coupling is performed in the presence of base, preferably a base selected from triethylamine, diisopropylethylamine and pyridine; preferably the base is triethylamine ($Et_3N$).

According to one embodiment, the coupling may be performed in the presence of a suitable solvent such as but not limited to DCM, acetonitrile or methanol, or neat; preferably in DCM.

According to one embodiment, the coupling is preferably performed at room temperature for 16 h.

The invention is further directed to the use of the compounds of the invention or pharmaceutically acceptable tautomers, salts and solvates thereof as OCT inhibitors.

Accordingly, in another aspect, the invention relates to the use of these compounds or tautomers, salts and solvates thereof for the synthesis of pharmaceutical active ingredients, such as OCT inhibitors.

According to a further feature of the present invention there is provided a method for modulating OCTs activity, in a patient, preferably a warm-blooded animal, and even more preferably a human, in need of such treatment, which comprises administering to said patient an effective amount of compound of the present invention, or a pharmaceutically acceptable tautomer, salt and solvate thereof.

According to a further feature of the present invention there is provided the use of a compound of the invention or a pharmaceutically acceptable tautomer, salt and solvate thereof for the manufacture of a medicament for modulating OCTs activity in a patient, in need of such treatment, which comprises administering to said patient an effective amount of compound of the present invention, or a pharmaceutically acceptable tautomer, salt and solvate thereof.

In one embodiment, the invention relates to the use of compounds of the invention, or pharmaceutically acceptable tautomers, salts and solvates thereof, for their antidepressant activity.

The compounds of the invention are therefore useful as medicaments, in particular for the prevention and/or treatment of mood-related disorders such as depressive disorders and anxiety disorders.

The invention further relates to a method for treatment and/or prevention of mood-related disorders such as depressive disorders and anxiety disorders; which comprises administering to a mammalian species in need thereof a therapeutically effective amount of the compound according to the invention or a pharmaceutically acceptable tautomer, salt or solvate thereof.

The invention further provides the use of a compound of the invention or a pharmaceutically acceptable tautomer, salt and solvate thereof for the manufacture of a medicament for treating and/or preventing mood-related disorders such as depressive disorders and anxiety disorders.

The invention also provides for a method for delaying in patient the onset of mood-related disorders such depressive disorders and anxiety disorders; comprising the administration of a pharmaceutically effective amount of a compound of the invention or pharmaceutically acceptable tautomer, salt and solvate thereof to a patient in need thereof.

Preferably, the patient is a warm-blooded animal, more preferably a human.

Mood-related disorders are for example depressive disorders and anxiety disorders.

The invention also provides pharmaceutical compositions comprising a compound of the invention or a pharmaceutically acceptable tautomer, salt and solvate thereof and at least one pharmaceutically acceptable carrier, diluent, excipient and/or adjuvant.

The invention also covers pharmaceutical compositions which contain, in addition to a compound of the present invention, a pharmaceutically acceptable tautomer, salt and solvate thereof as active ingredient, additional therapeutic agents and/or active ingredients.

Another object of this invention is a medicament comprising at least one compound of the invention, or a pharmaceutically acceptable tautomer, salt and solvate thereof, as active ingredient.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

EXAMPLES

Figure 1A:
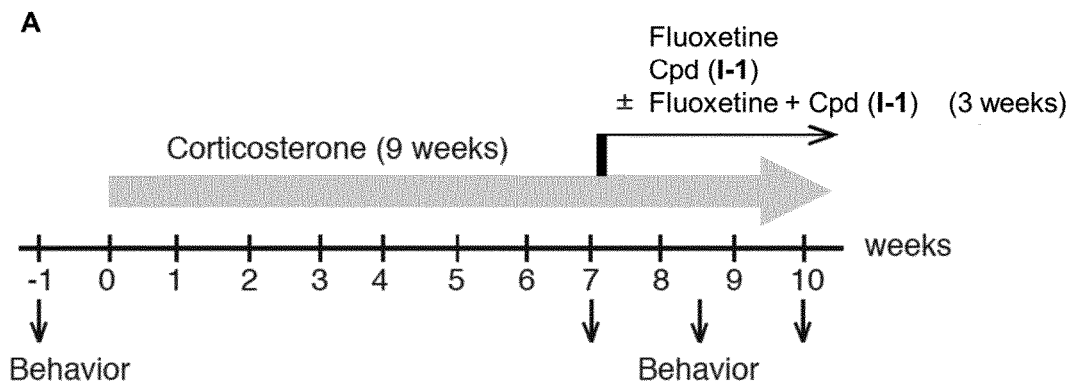
FIG. 1 is a combination of graph showing the repercussions of a long-term treatment with compound (I-1), fluoxetine or both compounds on depression-like behaviors, evaluated in mice in a validated chronic depression model. Experimental schemes for the corticosterone-induced depression (FIG. 1A) and social defeat (FIG. 1H) model are reported, wherein vertical arrows indicate the time points of behavioral testing. In the corticosterone depression model.
FIG. 1B presents the score of coat state.
FIG. 1C presents the sucrose preference as a percentage of the total amount of liquid ingested.
FIGS. 1D and 1E present the result of elevated O-maze test with respectively the time in open zone and the latency to enter into open zone.
FIG. 1F presents the exploration time of the objects in object location test.
FIG. 1G presents the interaction time in social interaction test. In the social defeat model.
FIG. 1I presents the time in interaction zone with target.

The present invention will be better understood with reference to the following examples. These examples are intended to representative of specific embodiments of the invention, and are not intended as limiting the scope of the invention.

The following abbreviations are used:
Å: ångström,
Ar: Argon,
ArH: Aromatic hydrogen,
Calcd.: Calculated
Cpd: Compound,
Conc.: concentrated,
DCM: Dichloromethane,
DMSO: Dimethyl sulfoxide,
eq.: Equivalent(s),
Et$_2$O: Diethyl ether,
EtOH: Ethanol,
g: Gram(s),
h: Hour(s),
HPLC: High Performance Liquid Chromatography,
HR-MS: High Resolution Mass Spectrometry,
L: Liter(s),
M: mol·L$^{-1}$,
MeOH: Methanol,
μL: Microliter(s),
mg: Milligram(s),
mL: Milliliter(s),
mmol: Millimole(s),
mM: mmol·L$^{-1}$,
min: Minute(s),
mol: Mole(s),
NMR: Nuclear magnetic resonance spectroscopy, TEA: Triethylamine,
THF: Tetrahydrofuran,
TLC: Thin layer chromatography,
TMS: Tetramethylsilane,
UV: UltraViolet.

I. Chemistry Examples

All air and moisture sensitive manipulations were performed either under nitrogen or in vacuo using standard Schlenk techniques. Anhydrous solvents (Et₂O, THF, toluene and hexane) were purchased from Sigma Aldrich. In addition, MeOH was stored over oven dried 4 Å molecular sieves under argon for at least 16 hours prior to use. All chemicals were purchased from Alfa Aesar, Sigma Aldrich and TCI Europe and were used without further purification unless otherwise stated.

Analytical thin layer chromatography (TLC) was performed with Merck SIL G/UV254 plates. Compounds were visualized by exposure to UV light or by dipping the plates in solutions of phosphomolybdic acid, ninhydrin or potassium permanganate followed by heating. Flash column chromatography was performed in air with silica gel 60 (Fluka).

NMR spectra were recorded on an ARX 250 or an Avance II 400 Bruker or an Avance II 500 Bruker spectrometers in the solvent indicated. 1H- and 13C-NMR chemical shifts (δ) are quoted in parts per million (ppm) relative to the TMS scale. Coupling constants (J) are reported in Hertz (Hz). The following abbreviations are used for the proton spectra multiplicities: s: singulet, d: doublet, t: triplet, q: quartet, qt: quintuplet, m: multiplet, br.: broad, dd: double doublet, dt: double triplet.

All mass spectrometry was carried out by the University of Paris Descartes mass spectrometry service. Infrared spectra (bands in cm⁻¹) were recorded on a Perkin-Elmer Spectrum one spectrophotometer using a diamond ATR Golden Gate accessory. HPLC purification was done using a Gilson analytical instrument.

The intermediates and compounds described below were named using ChemBioDraw® Ultra version 12.0 (PerkinElmer).

I.1. Synthesis of Intermediate Compounds

I.1a. Intermediates of Formula (III)

Intermediate (III-1):
4-chloro-1-isopropylquinolin-1-ium Iodide

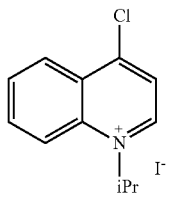

4-chloroquinoline (1.7 g, 10.39 mmol) was refluxed with iodopropane (7 mL, 70.12 mmol) for 48 h. The reaction mixture was cooled to room temperature and Et₂O was added. The mixture was triturated then filtered. The residue was washed successively with dry acetone (2×15 mL) and with Et₂O (4×25 mL) to give the title compound (1.1 g, 31%) as a brown solid. The product (III-1) is 83% pure and was used without further purification. 1H-NMR (500 MHz, DMSO-d6) δH: 9.17 (d, 1H, J=6.5 Hz, ArH), 8.85 (d, 1H, J=6.5 Hz, ArH), 8.71 (d, 1H, J=9.1 Hz, ArH), 8.45 (d, 1H, J=8.2 Hz, ArH), 8.32 (dd, 1H, J=7.1, 9.1 Hz, ArH), 8.12 (dd, 1H, J=7.1, 8.2 Hz, ArH), 5.83 (q, 1H, J=6.6 Hz, CHCH3), 1.71 (d, 6H, J=6.6 Hz, CHCH3). 13C-NMR (500 MHz, DMSO-d6) δC: 144.1, 136.6, 136.2, 134.5, 133.7, 132, 131.4, 119.3, 116.6, 57.4, 22 (×2). HR-MS (ESI(+), m/z, MeOH): calcd. for C12H13NI [M]⁺ 298.0087; found: 298.0086.

I.1.b. Intermediates of Formula (IV)

Intermediate (IV-1):
1-isopropyl-6-methoxy-2-methylquinolin-1-ium iodide

Step 1: 1-isopropyl-6-methoxyquinolin-1-ium iodide

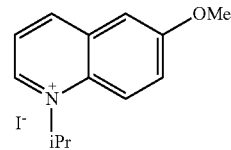

4-chloroquinoline (5 g, 31.40 mmol) was refluxed with iodopropane (15.6 mL, 157 mmol) for 48 h. The reaction mixture was cooled to room temperature and Et₂O was added. The mixture was triturated then the residue was washed with Et₂O to give the title compound (9.4 g, 93%) as a solid. 1H-NMR (500 MHz, DMSO-d6) δH: 9.44 (dd, 1H, J=1.5, 6.0 Hz, ArH), 9.11 (d, 1H, J=8.4 Hz, ArH), 8.67 (d, 1H, J=9.9 Hz, ArH), 8.15 (dd, 1H, J=6.0, 8.3 Hz, ArH), 9.44 (dd, 1H, J=1.5, 6.0 Hz, ArH), 7.95 (d, 1H, J=3.0 Hz, ArH), 7.90 (dd, 1H, J=7.3, 9.0 Hz, ArH), 5.86 (md, 1H, J=6.1, 6.6 Hz, CHCH3), 1.71 (d, 6H, J=6.5 Hz, CHCH3). 13C-NMR (250 MHz, DMSO-d6) δC: 158.9, 145.1, 143.1, 133.2, 131.8, 127.5, 122.6, 120.2, 108.6, 57.3, 56.4, 22.2 (×2). HR-MS (ESI(+), m/z, MeOH): calcd. for C13H16NO [M]⁺ 202.1226; found: 202.1224.

Step 2: 1-isopropyl-6-methoxy-2-methylquinolin-1-ium iodide (IV-1)

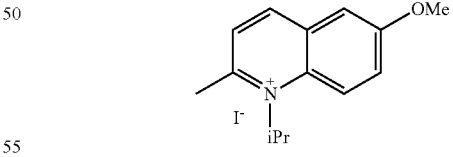

Following a procedure of Bradley and Jeffrey (Bradley, W. and Jeffrey, S. J., Chem. Soc., 1954, 2770-2778), 1-isopropyl-6-methoxyquinolin-1-ium iodide (10 g, 29.15 mmol) was added over 5 min to a solution of MeMgBr (3 M in DCM, 19.43 mL, 58.3 mmol) at 0° C. The reaction mixture was stirred at this temperature for 1 h and an additional 2 h at room temperature. Water was added slowly, followed by a solution of conc. HCl until two layers resulted then ammonium chloride and finally sufficient ammonia was added to make the solution alkaline. The organic layer was washed with water, dried over MgSO4 and concentrated in vacuo to give the dihydroquinoline (6.02 g) which was directly engaged for the next step without purification. The dihydroquinoline was refluxed in EtOH (40 mL) with iodine (9.6 g) for 15 min, the reaction mixture was then cooled to room temperature. The resulting residue was filtered was washed with EtOH and Et$_2$O to give the title compound (IV-1) (9.2 g, 88%). 1H-NMR (500 MHz, DMSO-d6) δH: 8.93 (d, 1H, J=8.6 Hz, ArH), 8.65 (d, 1H, J=9.9 Hz, ArH), 8.04 (d, 1H, J=8.5 Hz, ArH), 7.85 (d, 1H, J=3.1 Hz, ArH), 7.74 (d, 1H, J=8.5 Hz, ArH), 5.65 (t, 1H, J=6.0 Hz, CHCH3), 3.99 (s, 3H, CH3), 1.85 (d, 6H, J=6.5 Hz, CHCH3). 13C-NMR (250 MHz, DMSO-d6) δC: 157.9 (×2), 144.2, 132.7, 131.3, 126.2, 125.3, 122.2, 109.0, 57.9, 56.1, 23.4, 20.4 (×2). HR-MS (ESI(+), m/z, MeOH): calcd. for C14H18NO [M]$^+$ 216.1383; found: 216.1381.

I.1.c. Compounds of Formula (II)

Compound (II-1): (Z)-1-isopropyl-4-((1-isopropyl-6-methoxyquinolin-2(1H)-ylidene)methyl)quinolin-1-ium iodide

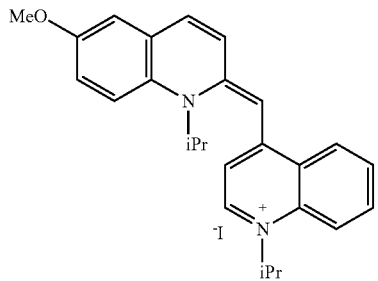

This compound was prepared following a procedure previously described by Lartia et al. (Lartia et al., Chem. Eur. J., 2006, 12, 2270-2281) with some modifications. Triethylamine (89.4 μL, 0.64 mmol, 2.2 eq) was added to 1-isopropyl-6-methoxy-2-methylquinolin-1-ium iodide (IV-1) (0.1 g, 0.29 mmol) solubilized in DCM (10 mL) and the mixture was stirred 15 min until color change (yellow to orange). 4-chloro-1-isopropylquinolin-1-ium iodide (III-1) (106 mg, 0.32 mmol) in DCM (5 mL, very slightly soluble) was added. The mixture turned blue purple rapidly and stirred was continued at room temperature for 16 h. The reaction mixture was concentrated until 5 mL and the residue was purified by flash chromatography using DCM-MeOH step gradient solvent system as an eluent to give a violet solid (198 mg, 92%). 1H-NMR (500 MHz, Acetone-d6) δH: 8.41 (dd, 1H, J=1.5, 8.4 Hz, ArH), 8.22 (d, 1H, J=9.4 Hz, ArH), 8.18 (m, 2H, ArH), 8.15 (d, 1H, J=7.6 Hz, ArH), 8.07 (d, 1H, J=8.9 Hz, ArH), 7.87 (ddd, 1H, J=1.5, 7.0, 8.9 Hz, ArH), 7.58 (dd, 1H, J=7.0, 8.4 Hz, ArH), 7.52 (d, 1H, J=3.0 Hz, ArH), 7.46 (dd, 1H, J=3.0, 9.4 Hz, ArH), 7.44 (d, 1H, J=7.5 Hz, ArH), 6.53 (s, 1H, CH), 5.6 (hept, 1H, J=7.1 Hz, CH), 5.31 (hept, 1H, J=6.6 Hz, CH), 3.97 (s, 3H, OCH3), 1.93 (d, 6H, J=7.1 Hz, CHCH3), 1.66 (d, 6H, J=6.6 Hz, CHCH3). 13C-NMR (250 MHz, DMSO-d6) δC: 156.3, 154.3, 146.7, 137.8, 137.7, 136.9, 133.2, 132.5, 127.9, 125.8, 125.5, 123.7, 123.1, 121.3, 120.1, 116.5, 109.8, 107.7, 95.4, 56.1, 55.7, 51.1, 21.5 (×2), 20.2 (×2). HR-MS (ESI(+), m/z, H$_2$O/CH$_3$CN): calcd. for C$_{26}$H$_{29}$N$_2$O [M]$^+$ 385.2274; found: 385.2261. HPLC (ACE Excel 2C18-Amide 0.2 mL/min) CH$_3$CN 0.01% HCOOH/CH$_3$CO$_2$NH$_4^+$ 10 mM pH=4.6.

Compound (II-2): (Z)-1-isopropyl-4-((1-isopropyl-6-methoxyquinolin-2(1H)-ylidene)(methoxy)methyl)quinolin-1-ium Iodide

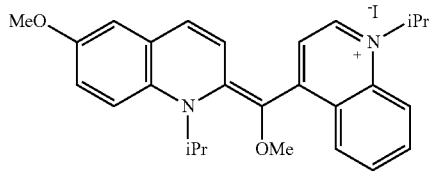

This compound was obtained as a secondary product of the synthesis used to obtain compound (II-1) described above. It was purified by flash chromatography using DCM-MeOH step gradient solvent system as an eluent to give a violet solid (90 mg, 42%). MS (ESI(+), m/z, H$_2$O/CH$_3$CN): 415.

1.2. Synthesis of Compounds of Formula (I)

Example 1: (Z)-1-isopropyl-4-((1-isopropyl-6-methoxy-3,4-dihydroquinolin-2(1H)-ylidene)methyl)quinolin-1-ium Iodide (I-1)

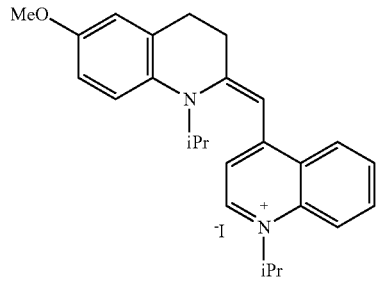

This compound was prepared following a procedure previously described by Foucout et al. (Foucout et al., Org. Biomol. Chem., 2009, 7, 3666-3673) with some modifications. (Z)-1-isopropyl-4-((1-isopropyl-6-methoxy-4a,8a-dihydroquinolin-2(1H)-ylidene) methyl)quinolin-1-ium iodide (II-1) with Et$_3$NHI salts (75 mg, 0.1 mmol, 1 eq.) was dissolved in a mixture of water (4 mL) and CH$_3$CN (4 mL) deaerated with nitrogen. Na$_2$S$_2$O$_4$ (88 mg, 0.5 mmol) was added and the mixture was stirred in darkness, at room temperature for 2 h until the color turn red. The same amounts of Na$_2$S$_2$O$_4$ (88 mg, 0.5 mmol) were added and the mixture was stirred 2 h more. The reaction mixture was first concentrated to eliminate CH$_3$CN then lyophilized. The red powder was solubilized in dry acetone, filtered under celite S45 and filtrate was concentrated to give red oil. The oil was purified by flash chromatography using DCM-MeOH (95/5) to give a hygroscopic red solid, which was lyophilized in an acetone/water mixture (1/10) to obtain a red powder (73 mg, 84%) which was stored at 5° C. under Ar. 1H-NMR (500 MHz, DMSO-d6) δH) δH: 8.8 (d, 1H, J=7.1 Hz, ArH), 8.65 (dd, 2H, J=1.7, 8.8 Hz, ArH), 8.41 (d, 1H, J=8.9 Hz, ArH), 8.07 (ddd, 1H, J=1.7, 7, 8.9 Hz, ArH), 7.83 (dd, 1H, J=7, 8.8 Hz, ArH), 7.42 (d, 1H, J=7.1 Hz, ArH), 7.34 (d, 1H, J=8.9 Hz, ArH), 6.9 (d, 1H, J=2.9 Hz, ArH), 6.84 (dd, 1H, J=2.9, 8.9 Hz, ArH), 6.55 (s, 1H, CH), 5.54 (hept, 1H, J=6.4 Hz, CH), 5.03 (hept, 1H, J=6.8 Hz, CH), 3.77 (s, 3H, OCH3), 3.11

(q, 4.5H, J=7.3 Hz, 3 eq $^+$NH(CH2CH3)$_3$), 3.1 (q, 4.5H, J=7.3 Hz, 3 eq $^+$NH(CH2CH3)$_3$), 3.06 (d, 1H, J=6.7 Hz, CH), 2.67 (dd, 2H, J=5.8, 6.7 Hz, CH2), 1.62 (d, 6H, J=6.4 Hz, CHCH3), 1.55 (d, 6H, J=6.8 Hz, CHCH3), 1.18 (t, 13.5H, J=7.3 Hz, 1.5 eq $^+$NH(CH2CH3)$_3$). 13C-NMR (500 MHz, DMSO-d6) δC: 159.6, 155.5, 153.4, 140, 137.4, 133.7, 133.4, 131.7, 127.4, 127, 126.3, 120.3, 117.7, 116.5, 112.7, 111.6, 92.9, 55.3, 53.7, 51.3, 45.8 ($^+$NH(CH2CH3)$_3$), 29.4, 25.1, 21.8 (×2), 20.4 (×2), 8.6 ($^+$NH(CH2CH3)$_3$). HR-MS (ESI(+), m/z, H$_2$O/CH$_3$CN): calcd. for $C_{26}H_{31}N_2O$ [M]$^+$ 387.2431; found: 387.2410. HPLC (ACE Excel 2C18-Amide 0.2 mL/min) CH$_3$CN 0.01% HCOOH/CH$_3$CO$_2^{-NH_4^+}$ 10 mM pH=4.6.

Example 2: (Z)-1-isopropyl-4-((1-isopropyl-6-methoxy-3,4-dihydroquinolin-2(1H)-ylidene)(methoxy)methyl)quinolin-1-ium Iodide (I-2)

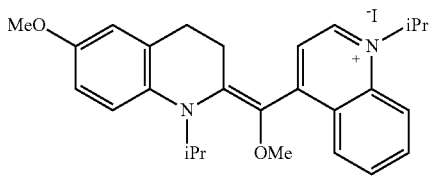

Compound (I-2) may be obtained by the same method as described for compound (I-1).

II. Biology Examples

Statistics. PRISM (GraphPad Software, San Diego, Calif., USA) 6.0 (SAS Institute, Cary, N.C., USA) were used for statistical calculations. For coat state, sucrose preference, O-maze, object location test, social interaction, microiontophoretic electrophysiology and Western blot experiments, data were analyzed using two-way or three-way analysis of variance (ANOVA) followed by Fisher's Protected LSD test. Statistical significance was set at P<0.05.

II.1. Vitro Assay—Metabolic Conversion in Microsomal Fraction

Purpose. This assay aims at showing that the prodrugs of Formula (I) of the invention can be converted into their active form, i.e. oxidized compounds of Formula (II), through exposure to biological medium.

Method. Rat liver microsomes (pool, 10 mg protein/mL) were obtained from BD-Gentest (Le Pont de Claix, France). Typical incubations were performed in 200 μL of potassium phosphate buffer (0.1M, pH 7.4) containing microsomes (1 mg protein/mL), compounds (I-1) or (II-1) (100 μM) and a NADPH generating system (1 mM NADP, 20 mM glucose-6-phosphate, 2 u/mL of glucose-6-phosphate dehydrogenase) at 37° C. for 30 min. The reactions were stopped by adding one-half volume of CH3CN containing 8% CH$_3$COOH and the proteins were removed by centrifugation at 13000 g. HPLC-MS studies were performed on a Nexera X2 UPLC instrument (Shimadzu, Marne La Vallée, France) coupled to an EXACTIVE Orbitrap mass spectrometer (Thermo, Les Ulis, France), using an ACE Excel 2C18-Amide column (150×2.1 mm, 2.3 μm) with a gradient A+B starting at 20% B for 5 min then increasing linearly to 100% B in 15 min (A=10 mM ammonium acetate plus 0.1% HCOOH, pH 4.6, and B=CH$_3$CN/HCOOH (999:1)) at 200 μL/min, with a gradient from 80% A for 5 min then increasing linearly to 100% B in 15 min (A=10 mM ammonium acetate plus 0.1% HCOOH, pH 4.6; B=CH$_3$CN/HCOOH (999:1)) at 200 μL/min.

Mass spectra were obtained by electrospray ionization (ESI) in positive ionization mode detection under the following conditions: source parameters, sheeth gas, 15; auxiliary gas, 5; spray voltage, 3.2 kV; capillary temperature, 275° C.; and m/z range for MS recorded generally between 150 and 900. For all products, the indicated parent ions corresponded to [M+H]$^+$.

Results. Incubation with microsomes led to the metabolisation of compounds (I-1). Among obtained metabolites, compound (II-1) was identified after only 5 min of incubation.

II.2. In Vitro Assay—OCT Inhibition in Transfected Cells

Purpose. Evaluation of affinity of the active compounds of the invention, especially compound (II-1), at human OCT2.

Method. Uptake of [$^3$H]ASP+ (5 μM) in COS cells transfected with human OCT2 was evaluated for 20 min at 37° C. in the presence of increasing concentrations of compound (II-1). Tested concentrations: $1.10^{-9}$; $3.10^{-9}$; $1.10^{-8}$; $3.10^{-8}$; $1.10^{-7}$; $3.10^{-7}$; $1.10^{-6}$; $3.10^{-6}$ mol·L$^{-1}$.

Results and Discussion. (II-1): IC50=82 nM. This experiment showed that compound (II-1) of the invention has an inhibitory effect on the hOCT2-mediated transport of the model substrate ASP+. Affinity at hOCT2 appeared even improved compared to that of D24, with an IC50 of 82 nM, a value 3 to 4-fold less than that of D24 on human and rodent OCTs (Amphoux et al., Eur. J. Pharmacol., 2010, 634, 1-9), indicating that this category of compound is effective to target human OCTs.

II.3. In Vitro Assay—Selectivity for OCT Over Adrenoreceptors

Purpose. Evaluation of the affinity of active compounds of the invention, especially compound (II-1), at alpha-adrenoceptors.

Method. The displacement by compound (II-1) of binding of selective ligands of alpha adrenergic receptors 1D and 2C (0.2 nM [$^3$H]Prazosin and 2 nM [$^3$H]RX 821002, respectively) was evaluated for 60 min at 22° C. in CHO cells expressing the human recombinant adrenoceptors (Eurofins).

Results. These binding experiments on CHO cells expressing specific adrenoceptors subtypes showed that 1 μM of compound (II-1) inhibits 69% and 66% of binding of specific ligands at alpha 1D and alpha 2C adrenoceptors, respectively.

Based on Ki values for D24 established in previous studies (Amphoux et al., Eur. J. Pharmacol., 2010, 634, 1-9), these results suggest that the derivatives of the present invention markedly increased affinity and selectivity at hOCT2 compared to D24, while decreasing affinity for human adrenoceptors.

II.4. In Vivo Assay—Action on Long-Term Antidepressant Efficacy in Chronic Depression Model Purpose. The antidepressant-promoting action of the compounds of the invention was evaluated in vivo in mice using a chronic depression model or social defeat model, upon administration, either alone or in combination with a classical antidepressant, fluoxetine.

Material. Male C57BL6/J mice were used for the experiments. Most behavioral studies were performed during the inactive phase (09:00-13:00) with age-matched (8-16 weeks) mice. Animal care and experiments were conducted in accordance with the European Communities Council Directive for the Care and the Use of Laboratory Animals (2010/63/UE) and approved by the French ethical committee.

Methods

Corticosterone-induced depression. To induce a chronic depression-like state, individually housed mice were administered corticosterone (35 mg ml-1; Sigma-Aldrich) dissolved in 0.45% (wt/vol) hydroxypropyl-b-cyclodextrin (Sigma-Aldrich) as in (Bacq et al., Mol. Psychiatry, 2012, 17, 926-939). Fluoxetine (LKT laboratories; 15 mg per kg per day), or compound (I-1) (0.1 mg per kg per day) or a combination of both was administered intraperitoneally daily during the last 3 weeks of the corticosterone regimen. The mice were tested successively for coat sate, sucrose consumption, elevated O-maze, object location test and social interaction, before antidepressant treatment, and after 10 days and 3 weeks of treatment. The experimental scheme is represented on FIG. 1A.

Social defeat model. For social defeat, 8-week-old C57Bl/6J mice were submitted to social defeat stress for 10 consecutive days as described (Berton et al., Science, 2006, 311(5762), 864-8). Social interaction tests were performed 1 d after the last day of defeat and after 3 weeks of treatment with fluoxetine (15 mg per kg per day) or (I-1) (0.2 mg per kg per day). The experimental scheme is represented on FIG. 1H.

Figure 1B:
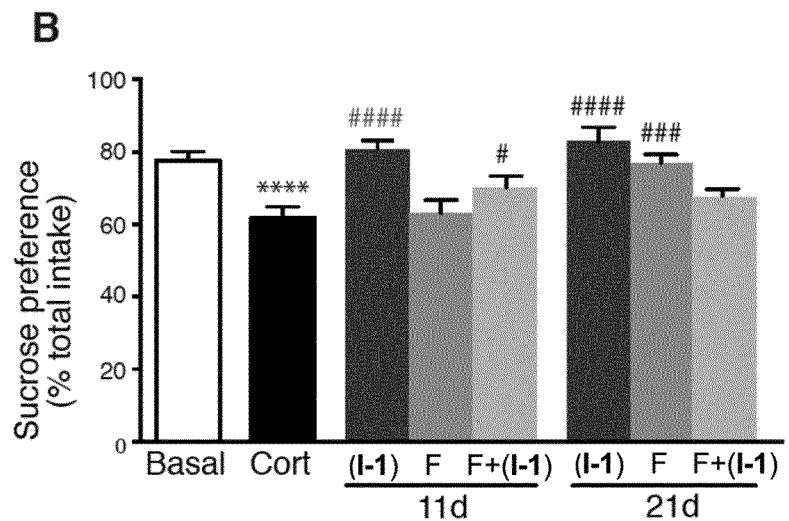

Coat state. The coat state of each animal was assessed weekly as a measure of motivation toward self-care. It was evaluated as the sum of the score of different parts of the body, ranging between 0 for a well-groomed coat and 1 for an unkempt coat for head, neck, dorsal/ventral coat, tail and forepaws/hindpaws (FIG. 1B).

Figure 1C:
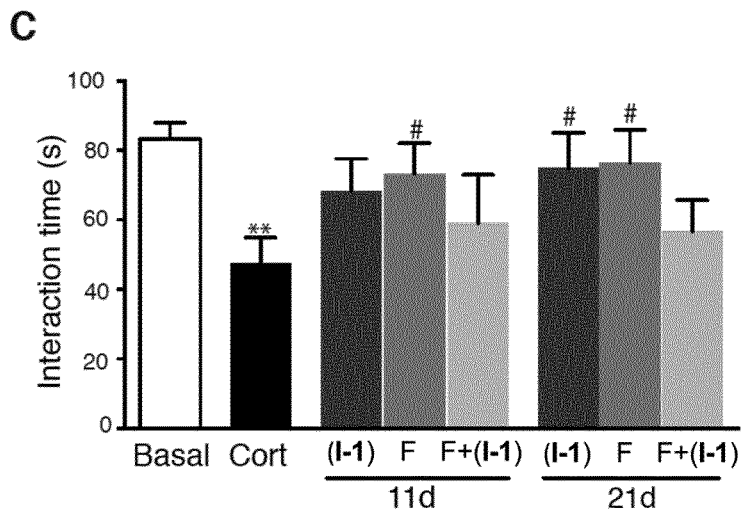

Sucrose preference test. Singled-house mice were first habituated for 48 h to drink water from two bottles. On the following 3 days, the mice could choose between a water bottle and a 1% (wt/vol) sucrose solution bottle, switched daily. Sucrose solution intake for 24 h was measured during the last 2 days and expressed as a percentage of the total amount of liquid ingested (FIG. 1C).

Figures 1D, 1E:
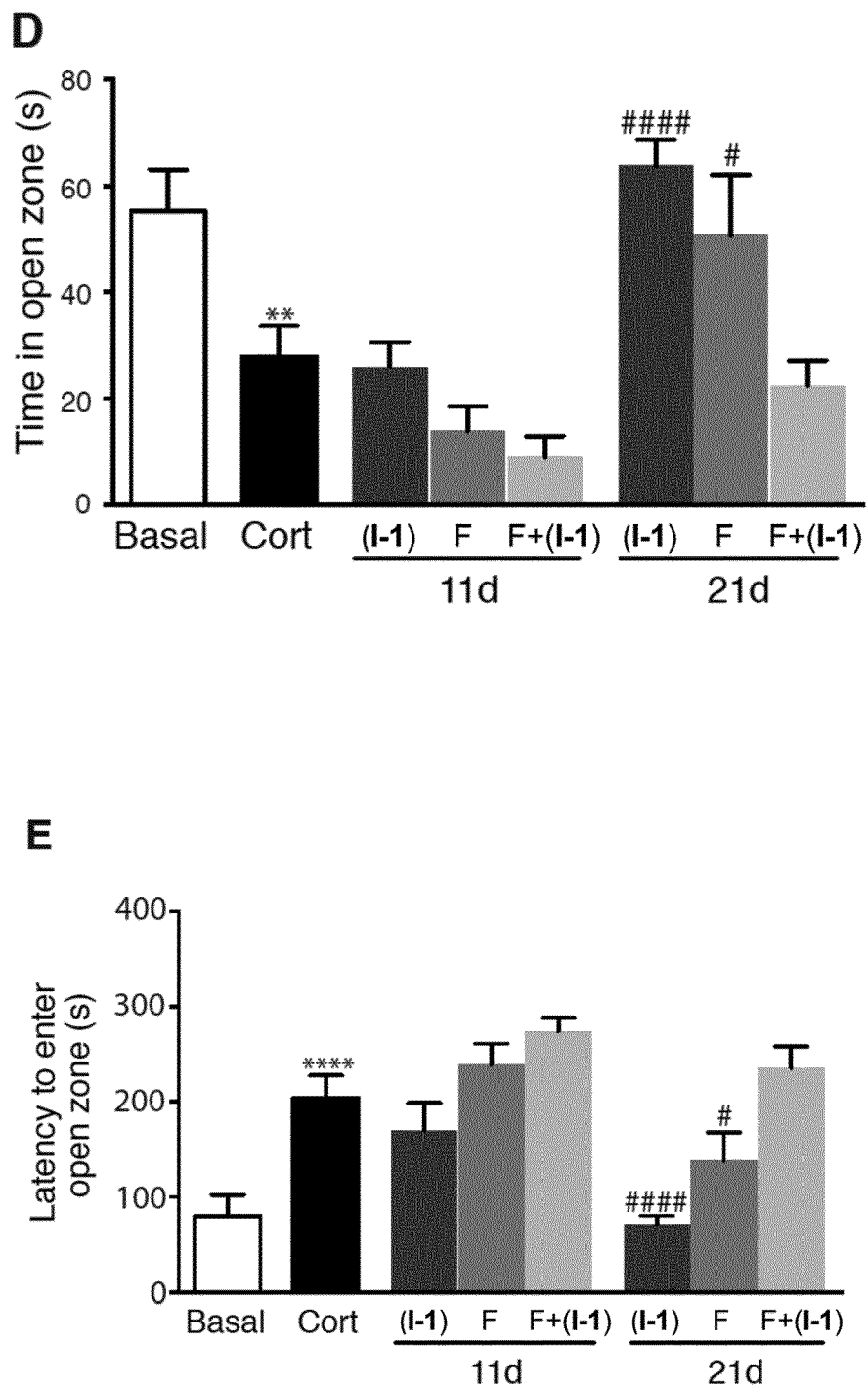

Elevated O-maze test. The elevated O-maze consisted of an annular runway positioned 40 cm above the floor and divided into two opposing 90° closed sectors and two 90° open sectors. The mice were individually placed in the closed sector and their behavior recorded over a 5-min period. The time spent in each sector and the number of sector entries (a sector entry was defined as all four of the paws being placed in a sector) were determined by video tracking (Viewpoint, Lyon, France) (FIGS. 1D and 1E).

Figure 1F:
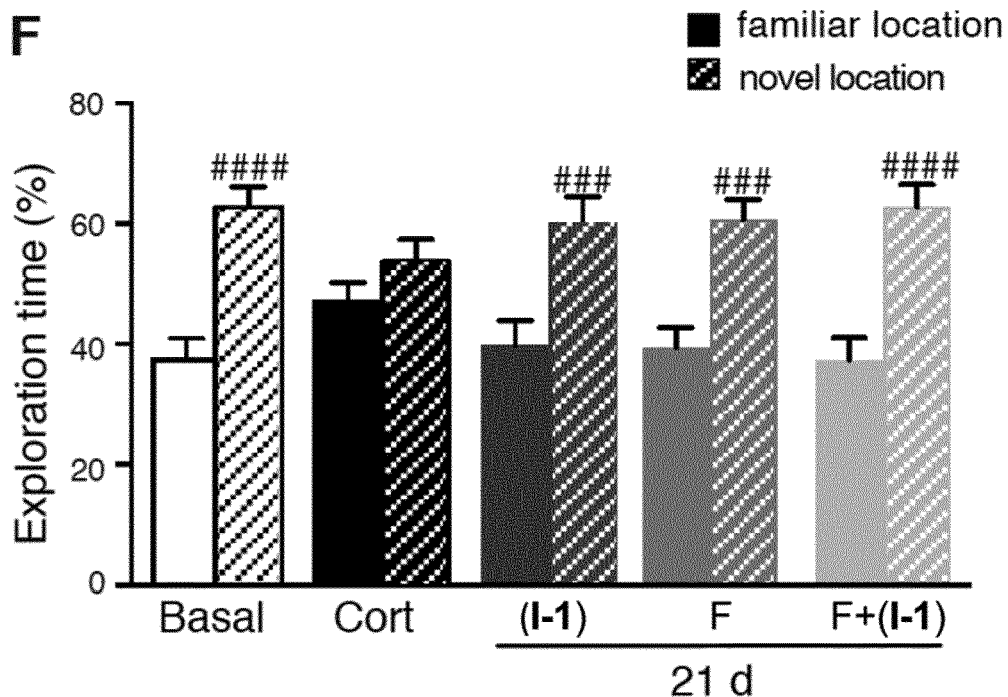
Figure 2A:
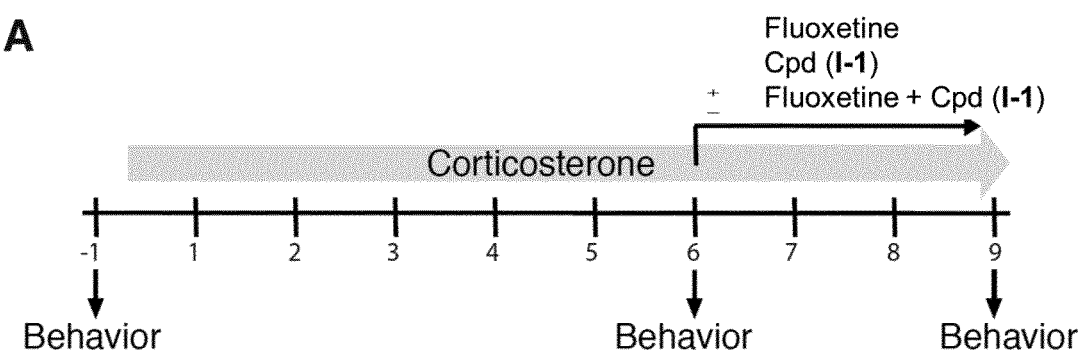
FIG. 2 is a combination of graphs showing the repercussions of a long-term treatment with compound (I-1), fluoxetine or both compounds on locomotor activity, depression-like behaviors and weight, evaluated in mice. Experimental scheme for the corticosterone-induced depression model (FIG. 2A) is reported, wherein vertical arrows indicate the time points of behavioral testing.
FIG. 2B reports results for open-field test regarding locomotor activity at periphery or in center as well as time in center.
FIG. 2C provides the exploration time in novel object recognition test.
FIG. 2D reports the evolution of mice weight over time.
Figure 2B:
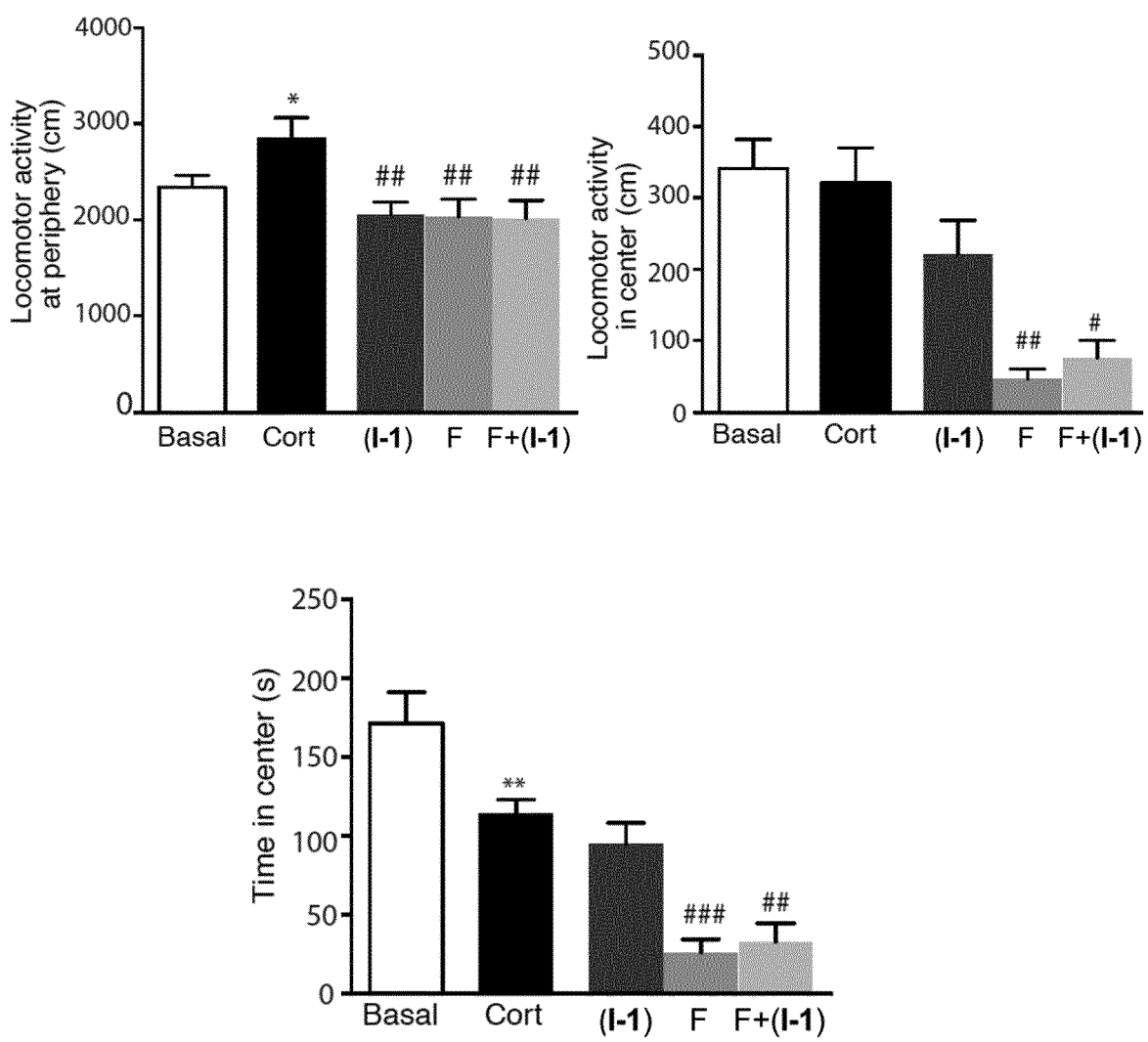
Figure 2C:
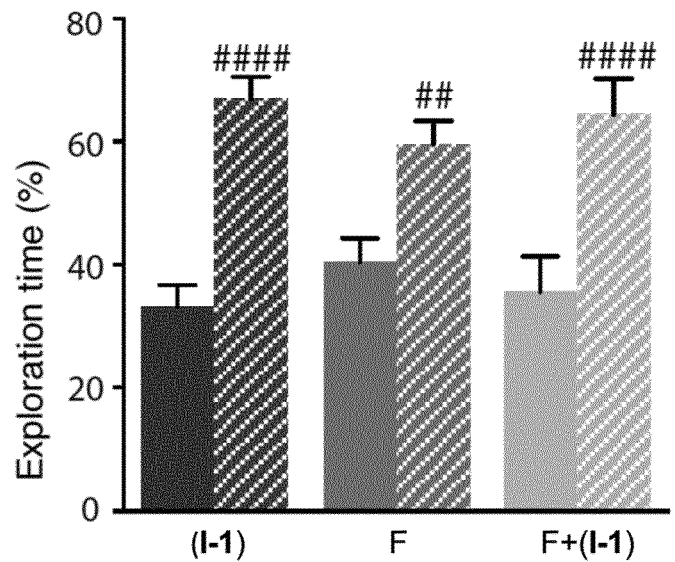

Object location (OLT) and novel object recognition (NOR) tests. The mice were habituated during two successive days to an open-field containing (OLT) or not (NOR) an intra-field cue (one wall covered with black and white stripes). Each mouse was allowed to freely explore the open-field for a 30-min period on day 1 and for two 10-min sessions separated by 5 h on day 2. On the third day, the test mouse was allowed to explore for 5 min two identical objects (5×2.5 cm) positioned in two adjacent corners of the open-field (acquisition phase) then returned to its home cage for 1 h. For the sample phase trial of the OLT, one of the two objects was displaced to the opposite corner of the open-field. For the sample phase trial of the NOR, one of the two objects was replaced by a novel object. The time spent exploring both objects was recorded over a 5-min session by video tracking (FIGS. 1F and 2C).

Figure 1G:
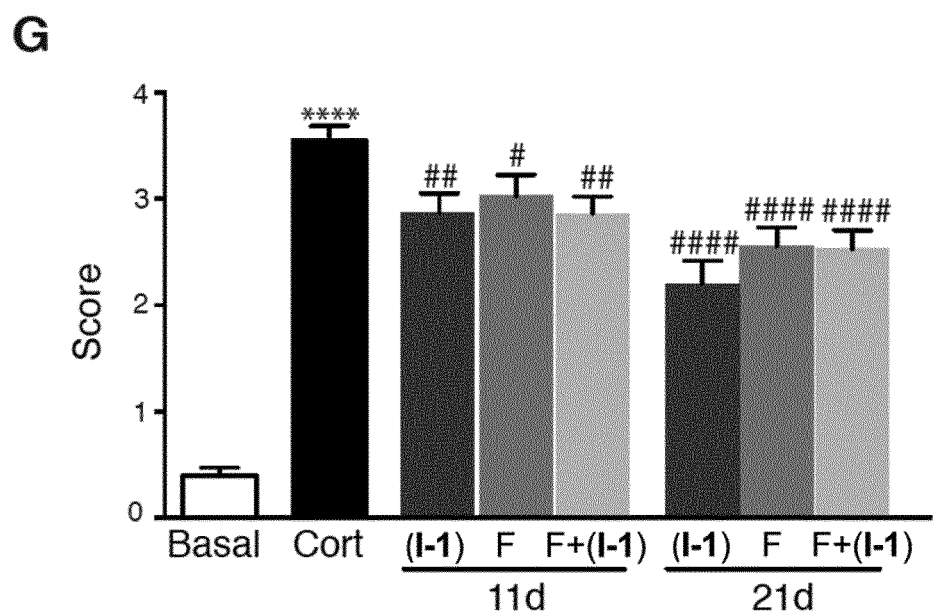
Figures 1H, 1I:
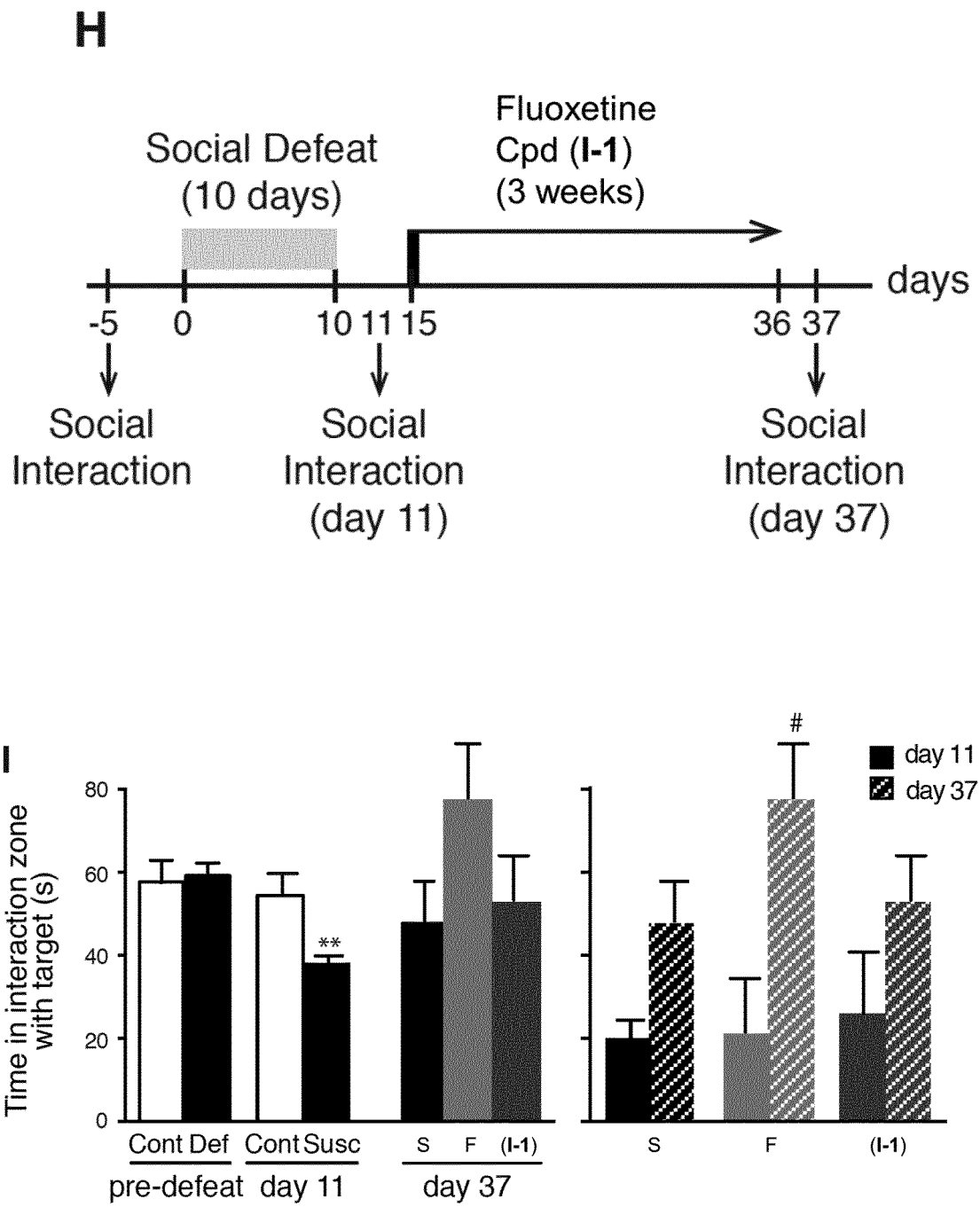

Social interaction test. The social interaction test was performed in a white open-field (42×42 cm) containing an empty wire mesh cage (10×6.5 cm) located at an extremity of the field in a low luminosity environment (25 lux). Each test mouse was allowed to explore the openfield for two consecutive sessions of 2.5 min. During the second session, an unfamiliar mouse was introduced into the cage. Between the two sessions, the test mouse was placed back into its home cage for approximately one minute. The time spent by the test mouse in the interaction zone, defined as an 8-cm-wide region surrounding the mesh cage, was measured in both sessions by video tracking (Viewpoint, Lyon, France) (FIGS. 1G and 1I).

Open-field test. The open field consisted of a white Plexiglas field (100×100×30 cm) with the center brightly illuminated (500 lux). General locomotor activity in the center and periphery of the open field were scored for 9 min. The time and number of entries in the center zone (60×60 cm) were evaluated as an index of anxiety-related response (FIG. 2B).

Figure 2D:
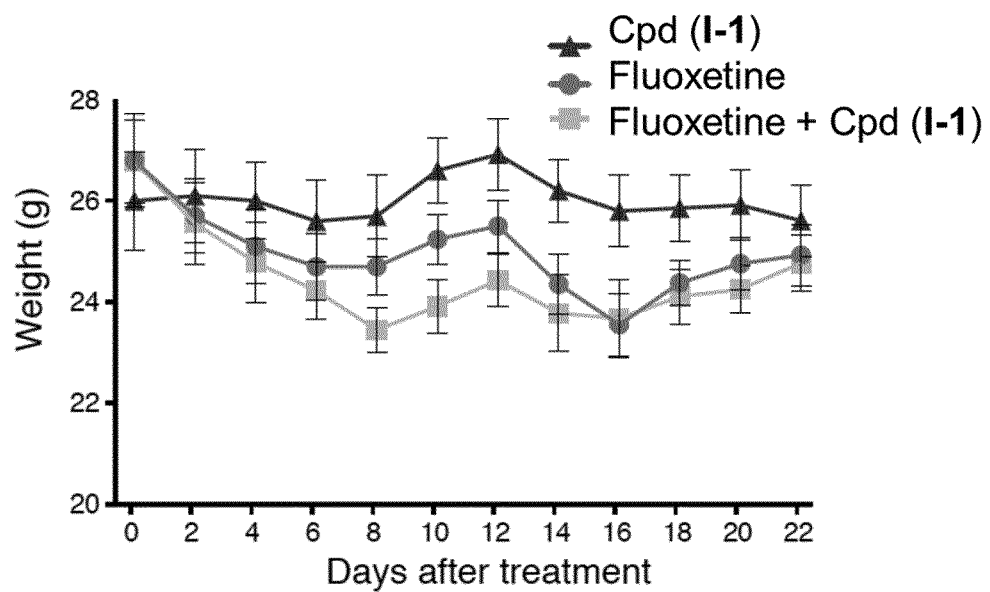

Effect on weight. The weight of tested mice was measured daily in the morning (FIG. 2D).

Results

The repercussions of a long-term treatment with compound (I-1), fluoxetine or both compounds on depression-like behaviors were evaluated in mice. The experimental schemes for the corticosterone-induced depression and social defeat model are represented on FIGS. 1A/2A and 1H respectively.

In the corticosterone depression model, one-way analysis of variance (ANOVA) (n=8-29) shows a significant effect of treatment on coat state (FIG. 1B, F7, 106=68.86; P<0.0001), sucrose preference (FIG. 1C, F7, 76=7.724; P<0.0001), time (FIG. 1D, F7, 66=9.408; P<0.0001) and latency (FIG. 1E, F4,45; P=0.0005) to enter the open zone of the elevated O-maze Fisher's post hoc tests which reveal significant differences between mice before and after corticosterone treatment (P<0.001, *P<0.001; ****P<0.0001).

Compound (I-1), fluoxetine or their combination improved coat state at both time points (FIG. 1B), compound (I-1) alone and combined with fluoxetine, but not fluoxetine alone, significantly increased sucrose preference at 11 days (FIG. 1C). Only compound (I-1) and fluoxetine, but not their combination, significantly increased sucrose preference at 21 days (FIG. 1C). Compound (I-1) and fluoxetine, but not their combination increased the time in the open zone of the elevated O-maze (FIG. 1D), and decreased the latency to enter this zone (FIG. 1E) after 21 days. Fisher's post-hoc test, #P<0.05, ##P<0.01, ###P<0.001, ####P<0.0001.

For the object location test (FIG. 1F), two-way ANOVA (n=8-10) show significant main effects of object on exploration time of the objects (F1, 84=68.88; P<0.0001). Fisher's post-hoc test reveals significant differences in exploration time of the displaced object (hatched) compared with the non-displaced object (full) before corticosterone as well as after all three treatments (###P<0.001, ####P<0.0001).

For the social interaction test (FIG. 1G), unpaired two-tailed Student's t-test (n=9-14) reveals significant effects on interaction time for corticosterone compared to basal state (**P<0.001, for fluoxetine at 11 days of treatment and for compound (I-1) and fluoxetine, but not their combination, at 21 days of treatment (#P<0.05).

For the open-field test (FIG. 2B), one-way analysis of variance (ANOVA) (n=9-11) reveals a significant effect of treatment on locomotor activity at periphery (F4, 45=4.191; P=0.0057), and locomotor activity (F4, 45=11.18; P<0.0001) and time (F4,45=20.81; P<0.0001) in the center. Fisher's post hoc tests reveal an effect of corticosterone on locomotor activity at periphery and time in the center (*P<0.05, **P<0.01). They also reveal a significant effect of compound (I-1), fluoxetine or both on locomotor activity at the periphery, and a significant increase in the compound (I-1)-treated group in time and activity in the center in the open field, compared to both fluoxetine-treated or to fluoxetine plus compound (I-1) treated groups, respectively (##P<0.01, ###P<0.001 compared to corticosterone).

For the novel object recognition test (FIG. 2C), one-way ANOVA (n=8-9) reveals similar performance after compound (I-1), fluoxetine, or the combination of both compounds (F5,46=12.12; P<0.0001) after 21 days of treatment. Fisher's post hoc test reveals significant differences in the exploration time of the novel object compared with the familiar object after all three treatments (##P<0.01, ####P<0.0001).

In the corticosterone depression model, one-way ANOVA (n=8-10) reveals no significant effect of compound (I-1) (F11, 108=0,2686; P=0,9902) or fluoxetine (F11,105=1.671; P=0,0902 but significant effect of the combination of both compounds (F11,93=2.059 P=0,0312) on weight (FIG. 2D).

Social defeat stress (Figure H) induced a profound social aversion (Mann-Whitney, P<0.01), which was reversed only by fluoxetine (17 mg/kg, n=8-9, main effect of treatment: two-way ANOVA F1,12=22.06; P<0.001) and not by compound (I-1) (0.1 mg/kg, n=8-9, two-way ANOVA F1,13=11.04; P<0.001). Fisher's post hoc tests reveal significant differences between mice before and after fluoxetine treatment (###P<0.001) and not after compound (I-1) treatment (FIG. 1I). All values are given as mean±s.e.m.

Discussion

Acute behavioral despair tests such as the forced-swim test (or Porsolt) are useful to screen antidepressants, but are not paradigms of depression, since they do not address the complete spectrum of cognitive and emotional dysfunctions found in this disorder.

Instead, a validated chronic depression model induced by corticosterone exposure was used, which models distinct symptoms of depression including anhedonia, anxiety, social withdrawal and memory impairment. Especially, the following symptoms may be assessed in mice:

| Symptom | Modeling in mice |
| --- | --- |
| Anhedonia (i.e. diminished interest or pleasure in everyday activities | Response to positive reward (sucrose preference test) |
| Social withdrawal | Social interaction test |
| Anxiety | Aversion for exposed places (elevated O-maze test) |
| Difficulty in performing minor tasks | Grooming, poor coat condition (coat state) |
| Diminished attention or thinking capacities | Attention, working or long-term memory tests (object location (OLT) and novel object recognition (NOR) tests) |

Importantly, in this model, the persistent behavioral anomalies induced by corticosterone can be improved by long-term, but not acute, antidepressant treatment, a characteristic shared with human depression.

In this chronic model of depression, the compound (I-1) shows rapid positive effects, as robust as classical antidepressants, on several behaviors such as sucrose preference, time in the anxiogenic zones of the open-field and elevated O-maze, social interaction and short-term memory (object location and novel object test), with a more rapid/faster action on anhedonia and better action on anxiety than fluoxetine (FIGS. 1 and 2).

In this chronic model of depression, the compound (I-1) also restored normal locomotor activity as fluoxetine, and did not decrease weight, as did fluoxetine, potentially because it may have less or no anorectic effects compared to fluoxetine (FIG. 2).

In contrast to its long-term effects, acute administration of compound (I-1) had no effect on locomotor activity or anxiety level, and a moderate but reproducible lowering (antidepressant-like) action on immobility time in the forced swim test.

II.5. In Vivo Assay—Toxicity

Purpose. Evaluation of blood parameters and cell death pathways in the brain in mice submitted to corticosterone-induced depression followed by a 3-week treatment with compound (I-1) as described in example 11.4 above.

Methods

Blood parameter evaluation. Blood was collected in lithium heparin after the 3 weeks of treatment. Hemograms were performed with a Siemens ADVIAZ 120 apparatus. For biochemistry, blood was centrifuged at 2000 g for 10 min at +4° C. and supernatant was analyzed with a COBAS 6000 (Roche) apparatus.

Cell death pathways in the brain—Western blots. Whole tissue extracts were prepared from bilateral punches (1-1.5 mm diameter; Miltex, York, Pa., USA) of brain regions from adult mice at basal state, submitted to corticosterone plus compound (I-1) or to corticosterone plus fluoxetine (as described in example II.4). Samples were homogenized by sonication in 2 vol of ice-cold phosphate-buffered saline containing 1% Triton X-100, protease inhibitors (Complete Protease Inhibitor Cocktail, Roche Diagnostics, Basel, Switzerland) and phosphatase inhibitors (Phosphatase Inhibitor Cocktail 3; Sigma-Aldrich). Protein concentrations were determined by Bradford's method. Proteins samples (15 µg) suspended in NuPage LDS sample buffer (Invitrogen, Carlsbad, Calif., USA) were separated by Bis-Tris sodium dodecyl sulfate polyacrylamide gel electrophoresis (10% gels) and transferred onto nitrocellulose membranes (Invitrogen). Transfer efficacy was controlled by Ponceau S staining. Unspecific binding sites were blocked in Tris-buffered saline containing 0.1% Tween-20 and 5% nonfat milk and membranes were immunoprobed with antibodies against β-actin (1/2500) and β-catenin (1/300) from Sigma-Aldrich or LC3B (1/5000) from Abcam. Membranes were incubated with infrared-labeled secondary antibodies (IRDye 700DX and IRDye 800CW; 1/5000; Rockland, Gilbertsvillle, Pa., USA). Immunoblotting was quantified with the Odyssey Infrared Imaging System and Application Software version 3.0 (LI-COR Biosciences, Lincoln, Nebr., USA).

Results

Measured blood parameters are reported in table 3 for control mice and for mice treated with fluoxetine, compound (I-1) or combination of both. Data are expressed as means±SEM (n=6). Significant effect of genotype (Student t test, * p<0.05,  p<0.01, *p<0.001).

TABLE 3

| | Control | Fluoxetine | H2-CYANOME | Fluoxetine + H2-CYANOME |
|---|---|---|---|---|
| Platelets | 182.5 ± 8.0 | 357 ± 57.2 | 254.1 ± 56.5 | 693.3 ± 336* |
| Leucocytes (g/L) | 5.47 ± 0.5 | 2.99 ± 0.08*** | 2.89 ± 0.4*** | 2.95 ± 0.3*** |
| Hematies (T/L) | 10.46 ± 0.4 | 8.5 ± 0.3** | 8.96 ± 0.5* | 8.49 ± 0.5* |
| Creatinine (mg/dl) | 0.38 ± 0.025 | 0.5 ± 0.04 | 0.43 ± 0.06 | 0.4 ± 0 |
| Urea (mg/dl) | 58 ± 2.3 | 64.2 ± 4.1 | 61.7 ± 1.9 | 78.2 ± 7.1* |
| AST (U/L) | 151.3 ± 14.4 | 584.2 ± 87.6** | 164.8 ± 6.2 | 227.7 ± 32.9 |
| ALT (U/L) | 39 ± 1.7 | 75.1 ± 12.4**** | 49.5 ± 4.2 | 58 ± 4.7 |
| ALP (U/L) | 66.7 ± 11.5 | 47.4 ± 6.2 | 53.3 ± 2.2 | 59.3 ± 2.2 |
| Total bilirubin (mg/dL) | 0.11 ± 0.02 | 0.12 ± 0.01 | 0.12 ± 0.01 | 0.1 ± 0.02 |

Data are expressed as means ± SEM (n = 6). Significant effect of genotype (Student t test, $*p < 0.05$, $p < 0.01$, $*p < 0.001$).

Figure 3:
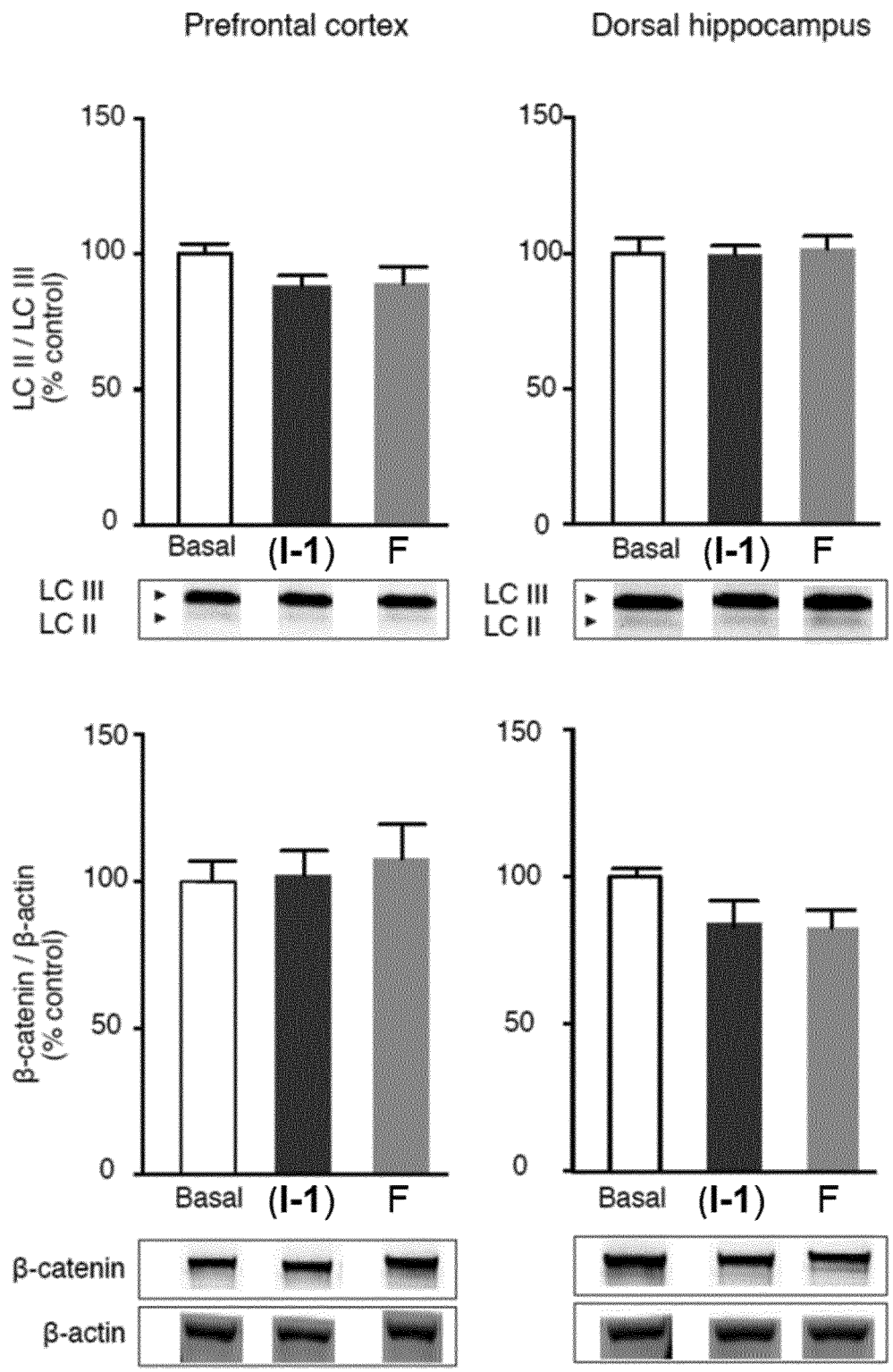
FIG. 3 is a combination of graphs showing the effects on cell death pathways in the brain of treatment with compound (I-1) or fluoxetine treatment, in a corticosterone-induced depression model. Quantitative Western blot are reported for LC3II and LC3I (top) and β-catenin and β-actin (bottom), in prefrontal cortex and hippocampus, as well as corresponding ratios.

Regarding cell death pathways in the brain, effects of compound (I-1) and of fluoxetine treatment on autophagy and proteasome pathways in the brain in the corticosterone induced depression model are reported in FIG. 3. Quantitative Western blot analysis show comparable LC3II/LC3I ratios (top) and β-catenin levels (bottom) after treatment with compound (I-1) or with fluoxetine, in prefrontal cortex and hippocampus. Results are given as mean±s.e.m.

Discussion

As evidenced with the blood parameters shows in table 3, prolonged administration of compound (I-1) shows similar effects than fluoxetine on blood cell counts, and hepatic and renal parameters with less hepatotoxicity.

Moreover, prolonged administration of compound (I-1) affects similar intracellular signaling pathways than fluoxetine in the brain, and does not alter autophagy and proteasome pathways in the brain (FIG. 3).

Altogether, the compounds of the invention thus could provide an effective and safe therapeutic alternative for depressive disorders including resistant depression as well as for other mood disturbances such as anxiety disorders.

Current antidepressants treatment shows important limitations in term of efficacy and speed of action. None of these currently existing antidepressants have as main target the OCTs, which represent novel targets for developing therapeutic agents for mood disorders. The compounds of the invention show strong efficacy when tested alone, improved speed of action on anhedonia and better action on anxiety compared to one of these common antidepressant, fluoxetine. Interestingly, the compounds of the invention appear to be less hepatotoxic than fluoxetine, and may have less anorectic effects.

The invention claimed is:

1. A compound of Formula (I)

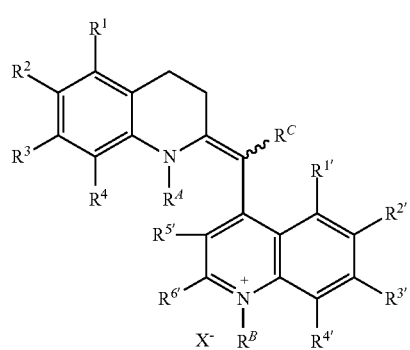

(I)

or a pharmaceutically acceptable tautomer, salt or solvate thereof, wherein:

⁓ represents a single bond linking $R^C$ to the double bond either with a (Z)- or (E)-stereochemistry;

X represents halo, acetate, trifluoroacetate or triflate;

$R^A$ and $R^B$ are independently selected from alkyl;

$R^C$ represents hydrogen or alkoxy;

$R^2$ and $R^3$ are independently selected from hydrogen, hydroxyl, alkoxy, halo, haloalkyl, haloalkyloxy, amino, alkylamino, aminoalkyl, alkyloxycarbonyl and COOH;

$R^1$, $R^4$, $R^{1'}$, $R^{2'}$, $R^{3'}$, $R^{4'}$, $R^{5'}$ and $R^{6'}$ are hydrogen;

wherein at least one of $R^2$, $R^3$ is other than hydrogen.

2. The compound according to claim 1, of Formula (Ia) or (Ib)

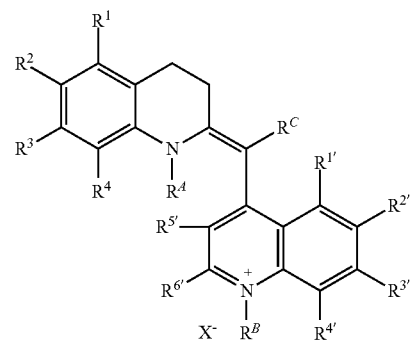

(Ia)

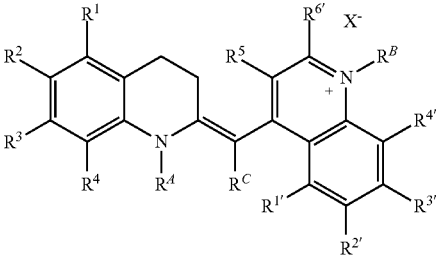

(Ib)

or a pharmaceutically acceptable tautomer, salt or solvate thereof, wherein X, $R^A$, $R^B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined in claim 1.

3. The compound according to claim 1, of Formula (I-1)

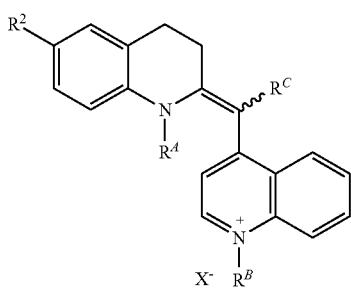

or a pharmaceutically acceptable tautomer, salt or solvate thereof, wherein ⌇, X, $R^A$, $R^B$, $R^C$ and $R^2$ are as defined in claim 1.

4. The compound according to claim 1, of Formula (Ia-1) or (Ib-1):

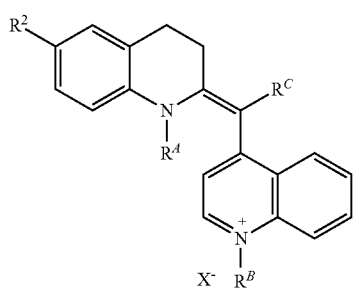

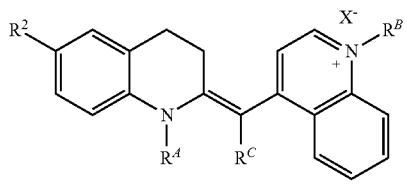

or a pharmaceutically acceptable tautomer, salt or solvate thereof, wherein X, $R^A$, $R^B$, $R^C$ and $R^2$ are as defined in claim 1.

5. The compound according to claim 1, selected from the group consisting of:
(Z)-1-isopropyl-4-((1-isopropyl-6-methoxy-3,4-dihydroquinolin-2(1H)-ylidene)methyl)quinolin-1-ium iodide;
(Z)-1-isopropyl-4-((1-isopropyl-6-methoxy-3,4-dihydroquinolin-2(1H)-ylidene)(methoxy)methyl)quinolin-1-ium iodide;
and a pharmaceutically acceptable tautomer, salt or solvate thereof.

6. A pharmaceutical composition comprising a compound according to claim 1, or a pharmaceutically acceptable tautomer, salt or solvate thereof, and at least one pharmaceutically acceptable carrier.

7. Medicament comprising a compound according to claim 1, or a pharmaceutically acceptable tautomer, salt or solvate thereof.

8. A method for the treatment of depressive disorders and anxiety disorders comprising administering a compound according to claim 1 or a pharmaceutically acceptable tautomer, salt or solvate thereof to a patient.

9. A method for inhibiting organic cation transporters (OCTs) comprising administering a compound according to claim 1 or a pharmaceutically acceptable tautomer, salt or solvate thereof.

10. Process for manufacturing a compound of Formula (I) according to claim 1 or a pharmaceutically acceptable tautomer, salt or solvate thereof, characterized in that it comprises the regioselective reduction of intermediate of Formula (II)

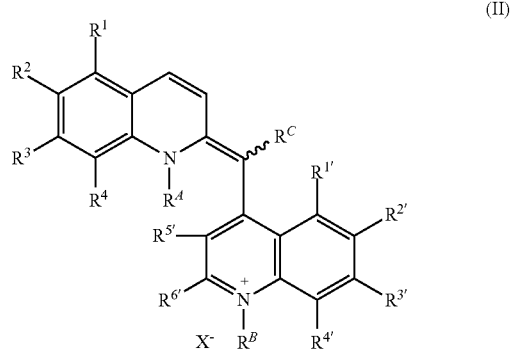

wherein ⌇, X, $R^A$, $R^B$, $R^C$, $R^1$, $R^2$, $R^3$, $R^4$, $R^{1'}$, $R^{2'}$, $R^{3'}$, $R^{4'}$, $R^{5'}$ and $R^{6'}$ are as defined in claim 1;

in presence of sodium dithionite ($Na_2S_2O_4$).

11. The process according to claim 10, comprising a preliminary step of synthesis of intermediate of Formula (II) comprising the coupling between intermediate of Formula (III) and intermediate of Formula (IV), in presence of a base:

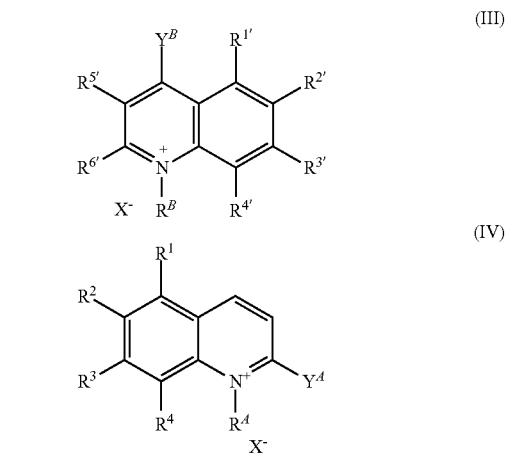

wherein $R^A$, $R^B$, $R^1$, $R^2$, $R^3$, $R^4$, $R^{1'}$, $R^{2'}$, $R^{3'}$, $R^{4'}$, $R^{5'}$ and $R^{6'}$ are as defined in claim 1; and $Y^A$ is —$CH_2R^C$, wherein $R^C$ is as defined in Formula (I); and $Y^B$ is hydrogen or a leaving group selected from halo, acetate, tosylate, mesylate and sulfate; $Y^B$ is halo; more;

or $Y^A$ is hydrogen or a leaving group selected from halo, acetate, tosylate, mesylate and sulfate; and $Y^B$ is —$CH_2R^C$, wherein $R^C$ is as defined in Formula (I).

12. A pharmaceutical composition comprising a compound according to claim 2, or a pharmaceutically acceptable tautomer, salt or solvate thereof, and at least one pharmaceutically acceptable carrier.

* * * * *